United States Patent
Ashvar et al.

(10) Patent No.: US 6,689,381 B2
(45) Date of Patent: Feb. 10, 2004

(54) LIPOSOMAL BENZOQUINAZOLINE THYMIDYLATE SYNTHASE INHIBITOR FORMULATIONS

(75) Inventors: Claudine S. Ashvar, Toluca Lake, CA (US); Su-Ming Chiang, Canoga Park, CA (US); David L. Emerson, Longmont, CO (US); Ning Hu, San Gabriel, CA (US); Gerard M. Jensen, Brea, CA (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 09/875,713

(22) Filed: Jun. 6, 2001

(65) Prior Publication Data

US 2002/0034538 A1 Mar. 21, 2002

Related U.S. Application Data

(60) Provisional application No. 60/210,592, filed on Jun. 9, 2000.

(51) Int. Cl.[7] ............................................... A61K 9/127
(52) U.S. Cl. ........................ 424/450; 264/4.1; 264/4.3; 514/248
(58) Field of Search ........................... 424/450; 264/4.1, 264/4.3, 4.6; 514/248

(56) References Cited

U.S. PATENT DOCUMENTS

| 4,753,788 A | | 6/1988 | Gamble |
| 4,755,388 A | * | 7/1988 | Heath |
| 4,963,367 A | * | 10/1990 | Ecanow |
| 5,663,337 A | | 9/1997 | Pendergast et al. |

OTHER PUBLICATIONS

PCT International Search Report for PCT International Application No. PCT/US01/18224 (Exhibit 3).

* cited by examiner

*Primary Examiner*—Gollamudi S. Kishore
(74) *Attorney, Agent, or Firm*—John P. White; Cooper & Dunham LLP

(57) ABSTRACT

Liposomal encapsulated benzoquinazoline thymidylate synthase inhibitor formulations are provided. The liposomes have improved pharmacokinetics and enhanced efficacy as anti-tumor agents compared to the free drug. The formulations include liposomes comprising at least one phosphatidylcholine, a cholesterol, and a benzoquinazoline thymidylate synthase inhibitor.

67 Claims, 5 Drawing Sheets

LIPOSOMAL BENZOQUINAZOLINE THYMIDYLATE SYNTHASE INHIBITOR FORMULATIONS

This application claims benefit of U.S. Provisional Application No. 60/210,592, filed Jun. 9, 2000, the contents of which are hereby incorporated by reference.

FIELD OF THE INVENTION

This invention relates to liposomal formulations containing benzoquinazoline thymidylate synthase inhibitors. Further, this invention relates to methods of manufacturing and of using such formulations.

BACKGROUND OF THE INVENTION

Liposomes are microscopic vesicles made, in part, from phospholipids which form closed, fluid-filled spheres when dispersed with water. A class of compounds, known as benzoquinazoline thymidylate synthase inhibitors, are known to have antitumor activity (U.S. Pat. No. 5,663,377). Described herein are liposomal formulations containing benzoquinazoline thymidylate synthase inhibitors.

SUMMARY OF THE INVENTION

The present invention provides for liposomal formulations comprising at least one phosphatidylcholine, a cholesterol, and a benzoquinazoline thymidylate synthase inhibitor.

DETAILED DESCRIPTION OF THE INVENTION

Figure 1:
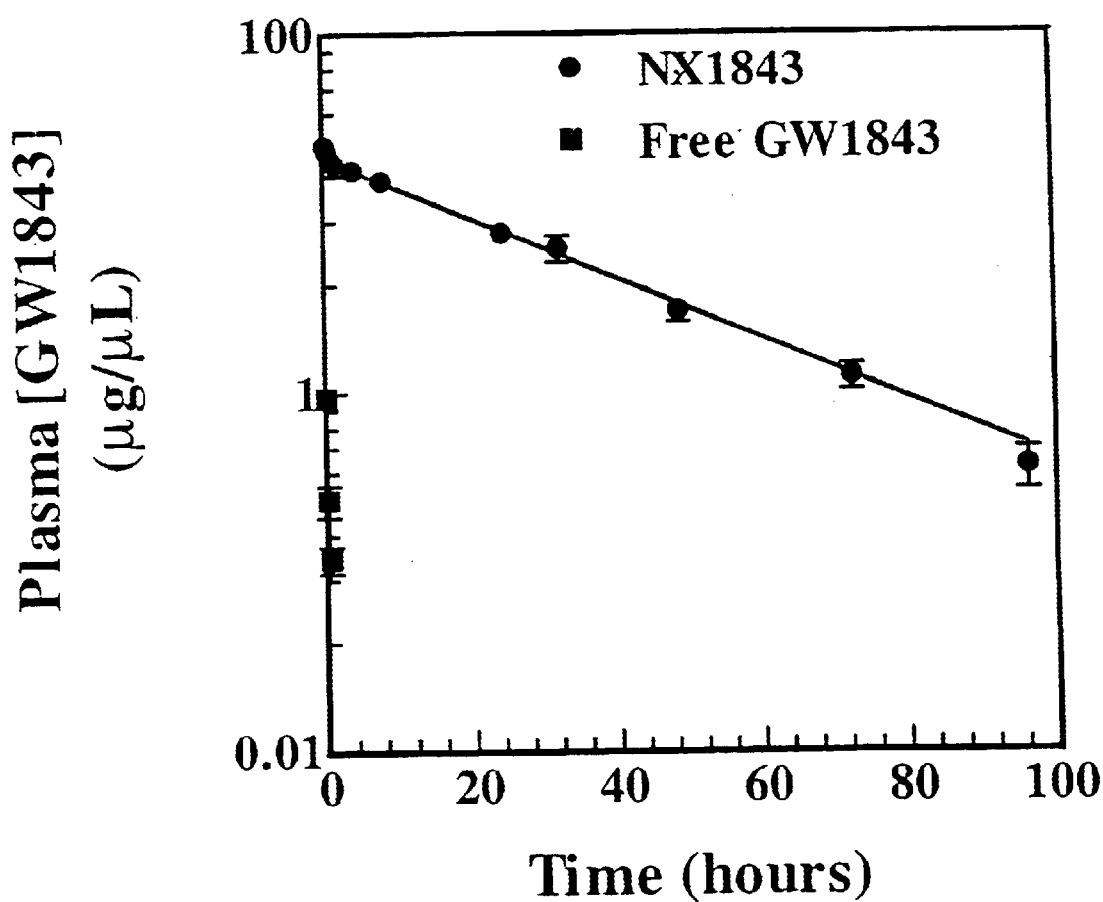
FIG. 1 depicts the log total plasma GW1843 concentration versus time curves (Mean±SD) following intravenous administration in male Sprague-Dawley rats of liposome encapsulated GW1843 (NX1843) or Free GW1843. NX1843 data fitted to a two phase exponential equation.

Formulations comprising benzoquinazoline thymidylate synthase inhibitors (BTSI) encapsulated in a liposome are provided as well as methods of their preparation. The formulations have pharmaceutical uses, including as antitumor or anti-viral agents. In addition, the liposomes have improved pharmacokinetics and enhanced efficacy as antitumor agents as compared to the free drug. The formulations include liposomes comprised of at least one phosphatidylcholine, a cholesterol and a BTSI.

Benzoquinazoline thymidylate synthase inhibitors of the present invention (herein referred to as compound(s) of the invention) are described in U.S. Pat. No. 5,663,337, Sep. 2, 1997, which is incorporated by reference in its entirety, in particular, column 1, line 37 to column 6, line 45, inclusive, are incorporated by reference at this location.

Accordingly, the present invention provides compounds of the formula (I)

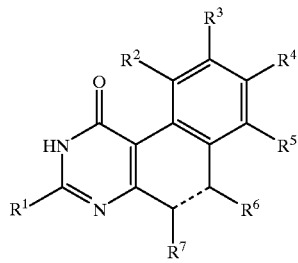

or a salt thereof, wherein the dotted line represents a single or double bond, $R^1$ is $C_{1-4}$ alkyl or amino optionally substituted by a $C_{1-4}$ alkyl, $C_{1-5}$ alkanoyl or benzyl group;

$R^2$, $R^3$, $R^4$ and $R^5$ are the same or different and each is selected from hydrogen, phenyl, halo, nitro, a group $S(O)_n R^8$ wherein n is the integer 0, 1 or 2 and $R^8$ is halo or is $C_{1-4}$ alkyl or a group $NR^9 R^{10}$ wherein $R^9$ and $R^{10}$ are both hydrogen, a group $NR^{11} R^{12}$ wherein $R^{11}$ and $R^{12}$ are the same or different and each is hydrogen or $C_{1-4}$ alkyl, a group $OR^{13}$ wherein $R^{13}$ is hydrogen or $C_{1-4}$ alkyl optionally substituted by halo;

a $C_{1-4}$ aliphatic group optionally substituted by a group $OR^{14}$ or $NR^{14} R^{15}$ wherein $R^{14}$ and $R^{15}$ are the sane or different and each is hydrogen or $C_{1-4}$ alkyl;

or two of $R^2$ to $R^5$ are linked together to form a benzo group, or one of $R^2$ to $R^5$ is a group —X—Y—$R^{16}$ wherein X is $CH_2$, $NR^{17}$, CO or $S(O)_m$ and m is 0, 1 or 2 and $R^{17}$ is hydrogen or a $C_{1-4}$ aliphatic group and Y is $CH_2$, $NR^{17'}$, O, or $S(O)_{m'}$, wherein m' is 0, 1 or 2 and $R^{17'}$ is hydrogen or a $C_{1-4}$ aliphatic group provided that X and Y are only the same when each is $CH_2$, or —X—Y—is a group —O—, —$NR^{17}$—, —CH=CH— or —N=N— wherein $R^{17}$ is as hereinbefore defined, $R^{16}$ is a $C_{1-4}$ aliphatic group or a 5- or 6-membered aromatic ring optionally substituted by a group $R^{18}$ at a position at least one carbon atom removed from that linked to Y, the 5- or 6-membered ring being optionally further substituted by a halo atom; and $R^{18}$ is halo, $C_{1-4}$ alkoxy, nitro, nitrile, $C_{1-4}$ alkyl optionally substituted by halo, halo or a group $COR^{19}$ wherein $R^{19}$ is hydroxy, $C_{1-4}$ alkoxy or $C_{1-6}$ alkyl optionally substituted by one or two carboxyl groups or $C_{1-12}$ esters thereof or $R^{19}$ is a group $NR^{20}R^{21}$ wherein $R^{20}$ and $R^{21}$ are the same or different and each is hydrogen or $C_{1-4}$ alkyl optionally substituted by hydroxy or $R^{19}$ is an amino acid group or an ester thereof in which the first nitrogen atom of the amino acid group may be linked to the 5- or 6-membered aromatic ring to form a further 5- or 6-membered heterocyclic ring or $R^{19}$ is an $C_{2-3}$ alkylene group linked to the 5- or 6-membered aromatic ring to form a further 5- or 6-membered ring;

$R^6$ and $R^7$ are the same or different and each is $C_{1-4}$ alkyl optionally substituted by hydroxy or $C_{1-4}$ alkoxy or together form a benzo group;

provided that at least one of $R^2$ to $R^7$ is other than hydrogen and that $R^4$ is not methoxy when $R^1$ is hydroxy or methyl.

By the term halo is meant fluoro, bromo, chloro and iodo.

By the term $C_{1-4}$ aliphatic group is meant a $C_{1-4}$ alkyl, alkenyl, or alkynyl group.

By the term amino acid group is meant naturally occurring amino acids.

Preferred amino acid groups include glycine, glutamic acid and polyglutamic and groups.

When the amino acid group is linked to the 5- or 6-membered aromatic ring, this is via a carbon atom of the aromatic ring adjacent to carbon to which $COR^{19}$ is attached.

Preferably the dotted line is a double bond.

Suitable substituents for the aromatic ring $R^{16}$ include halo, $C_{1-4}$ alkyl and $C_{1-4}$ alkoxy each optionally substituted by one to five halo atoms. Most suitably there are one or two substituents selected from fluoro, chloro, methyl, trifluoromethyl and methoxy, and preferably fluoro, or no substituents on the aromatic ring. In one preferred embodiment, —X—Y—$R^{16}$ is a group

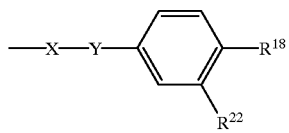

wherein $R^{18}$ is as hereinbefore defined and preferably a group $COR^{19}$ as hereinbefore defined and $R^{22}$ is hydrogen or fluoro.

In a further preferred embodiment X—Y—$R^{16}$ is a group

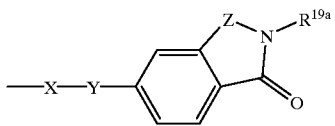

wherein $H_2NR^{19a}$ is a glutamic or polyglutamic acid group and Z is $CH_2$, S or O.

Suitably, $R^1$ is an amino group optionally substituted by one or two methyl or ethyl groups or $R^1$ is a methyl or ethyl group. Preferably $R^1$ is an amino or methyl group.

Suitably, at most only three, and preferably at most only two, of $R^2$ to $R^5$ are other than hydrogen and each is independently selected from hydrogen, halo, hydroxy, nitro, $C_{1-3}$ alkyl optionally substituted by hydroxy or $C_{1-2}$ alkoxy, $C_{1-3}$ alkoxy, amino optionally substituted by one or two methyl or ethyl groups, or a group S(O)n $R^{23}$ wherein n is 0, 1 or 2 and $R^{23}$ is a $C_{1-4}$ alkyl group or an amino group optionally substituted by one or two methyl or ethyl groups, or one of $R^2$ to $R^5$ is a group —X—Y—$R^{24}$ where $R^{24}$ is a group

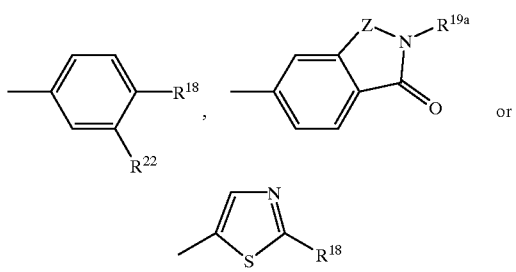

wherein $R^{18}$, $R^{19a}$, $R^{22}$ and Z are as hereinbefore defined. In one preferred embodiment $R^{18}$ is nitro or a group

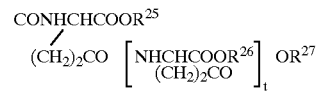

wherein $R^{25}$, $R^{26}$ and $R^{27}$ are the same or different and each is hydrogen or a $C_{1-4}$ alkyl group and t is an integer from 0 to 6. Preferably $R^{25}$, $R^{26}$ and $R^{27}$ are hydrogen and t is 0. Preferably Z is $CH_2$ or S.

Preferably one of $R^2$ to $R^5$ is a group —X—Y—$R^{24}$ as hereinbefore defined. Preferably $R^3$ is a group —X—Y—$R^{24}$.

Suitably $R^6$ and $R^7$ are the same or different and each is hydrogen, methyl, ethyl or methyl substituted by bromo, hydroxy or methoxy. Preferably $R^7$ is hydrogen and $R^6$ is methyl.

Preferably —X—Y— is a group — $SO_2NR^{17}$ or $CH_2NR^{17}$ wherein $R^{17}$ is as hereinbefore defined.

Suitably $R^{17}$ is hydrogen or a $C_{1-4}$ alkyl or alkenyl group and preferably $R^{17}$ is hydrogen or methyl.

One group of compounds of the present invention is that of the formula (Ia)

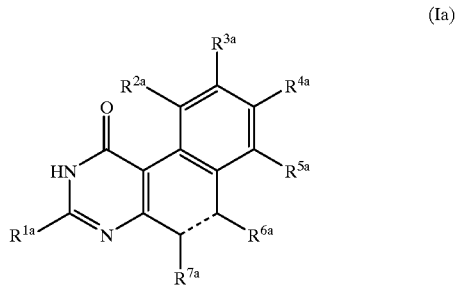

(Ia)

or a salt thereof, wherein the dotted line represents a single or double bond, $R^{1a}$ is $C_{1-4}$ alkyl or amino optionally substituted by a $C_{1-4}$ alkyl, $C_{1-5}$ alkanoyl or benzyl group; $R^{2a}$, $R^{3a}$, $R^{4a}$ and $R^{5a}$ are the same or different and each is selected from hydrogen, halo, nitro, a group $S(O)_n R^{8a}$ wherein n is the integer 0, 1 or 2 and $R^{8a}$ is halo or is a $C_{1-4}$ alkyl or amino group; a group $NR^{11}R^{12a}$ wherein $R^{11a}$ and $R^{12a}$ are the same or different and each is hydrogen or $C_{1-4}$ alkyl, a group $OR^{13a}$ wherein $R^{13a}$ is hydrogen or $C_{1-4}$ alkyl optionally substituted by halo, a $C_{1-4}$ aliphatic group optionally substituted by a group $OR^{14a}$ or $NR^{14a}R^{15a}$ wherein $R^{14a}$ and $R^{15a}$ are the same or different and each is hydrogen or $C_{1-4}$ alkyl, or one of $R^{2a}$ to $R^{5a}$ is a group —X—Y—$R^{16a}$ wherein X is $CH_2$, $NR^{17a}$, CO or $S(O)_m$ and m is 0, 1 or 2 and $R^{17a}$ is hydrogen or a $C_{1-4}$ aliphatic group and Y is $CH_2$, $NR_{17'a}$, O, or $S(O)_{m'}$, wherein m' is 0, 1 or 2 and $R^{17'a}$ is hydrogen or a $C_{1-4}$ aliphatic group provided that X and Y are only the same when each is $CH_2$, or —X—Y— is a group —$NR^{17a}$—, —CH=CN— or —N=N— wherein $R^{17a}$ as hereinbefore defined, $R^{16a}$ is a $C_{1-4}$ aliphatic group or an optionally substituted 5- or 6-membered aromatic ring substituted by a group $R^{18a}$ at a position at least one carbon atom removed from that linked to Y and $R^{18a}$ is nitro, nitrile, $C_{1-4}$ alkyl optionally substituted by halo, halo or a group $COR^{19a}$ wherein $R^{19a}$ is $C_{1-6}$ alkyl optionally substituted by one or two carboxyl groups or $C_{1-4}$ alkoxy, a group $CONR^{20a}R^{21a}$ wherein $R^{20a}$ and $R^{21a}$ are the same or different and each is hydrogen or $C_{1-4}$ alkyl or $R^{19a}$ is a glutamic or polyglutamic acid group or an ester thereof in which the first nitrogen atom of the glutamic or polyglutamic acid group may be linked to the 5- or 6-membered aromatic ring to form a further 5- or 6-membered heterocyclic ring; $R^{6a}$ and $R^{7a}$ are the same or different and each is $C_{1-4}$ alkyl optionally substituted by hydroxy or $C_{1-4}$ alkoxy or together form a benzo group, provided that at least one of $R^{2a}$ to $R^{7a}$ is other than hydrogen and that $R^{4a}$ is not methoxy when $R^{1a}$ is hydroxy or methyl.

A further group of compounds of the present invention is that of the formula (II)

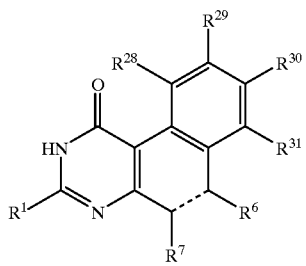

(II)

or a salt thereof, wherein $R^1$, $R^6$, $R^7$ and the dotted line are as hereinbefore defined and $R^{28}$ to $R^{31}$ are the same or different and each is selected from hydrogen, halo, nitro, a group $S(O)_nR^8$, a group $NR^{11}R^{12}$, a group $OR^{13}$, or a $C_{1-4}$ aliphatic group optionally substituted by a group $OR^{14}$ or $NR^{14}R^{15}$ wherein $R^8$, $R^{11}$, $R^{12}$, $R^{13}$, $R^{14}$ and $R^{15}$ are as hereinbefore defined, provided that $R^{28}$ to $R^{31}$ are not all hydrogen and that $R^{30}$ is not methoxy wherein $R^1$ is hydroxy or methyl.

A preferred group of compounds of the present invention is that of the formula (III):

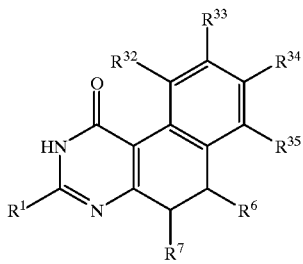

(III)

or a salt thereof, wherein $R^1$, $R^6$ and $R^7$ are as hereinbefore defined and $R^{32}$ to $R^{35}$ are the same or different and one is a group X—Y—$R^{16}$ and the others are the same or different and each is selected from hydrogen, halo, nitro, a group $S(O)_nR^8$, a group $NR^{11}R^{12}$, a group $OR^{13}$ or a $C_{1-4}$ aliphatic group optionally substituted by a group $OR^{14}$ or $NR^{14}R^{15}$, wherein X, Y, $R^8$, $R^{11}$, $R^{12}$, $R^{13}$, $R^{14}$, $R^{15}$ and $R^{16}$ are as hereinbefore defined.

A further preferred group of compounds of the present invention is that of the formula (IV):

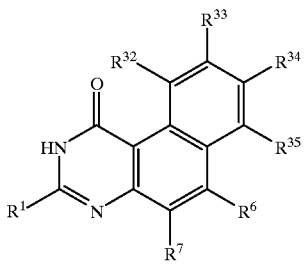

(IV)

wherein $R^1$, $R^6$, $R^7$ and $R^{32}$ to $R^{35}$ are as hereinbefore defined.

Preferably $R^{33}$ is a group X—Y—$R^{16}$ as hereinbefore defined.

Preferred compounds of the formula (I) include:
3-Amino-9-bromobenzo[f]quinazolin-1(2H)-one
3-Amino-9-ethynylbenzo[f]quinazolin-1(2H)-one
N-(4-((3-Amino-1,2,5,6-tetrahydro-1-oxobenzo[f]quinazolin-9-yl)sulfonamido)benzoyl)-L-glutamic acid
N-(4-((1,2,5,6-tetrahydro-3-methyl-1-oxobenzo[f]quinazolin-9-yl)-sulfonamido)benzoyl)-L-glutamic acid
N-(4-((1,2-Dihydro-3-methyl-1-oxobenzo[f]quinazolin-9-yl)sulfonamido)benzoyl)-L-glutamic acid
N-(4-(((1,2-Dihydro-3-methyl-1-oxobenzo[f]quinazolin-9-yl)methyl)amino)-2-fluorobenzoyl)-L-glutamic acid
N-(4(((1,2-Dihydro-3-methyl-1-oxobenzo[f]quinazolin-9-yl)methyl)amino)benzoyl)-L-glutamic acid
(S)-2-(5-(((1,2-Dihydro-3-methyl-1-oxobenzo[f]quinazolin-9-yl)methyl)amino-1-oxo-2-isoindolinyl) glutaric acid
9-((4-Acetylanilino)methyl)-3-methylbenzo[f]quinazolin-1 (2H)-one
3-Methyl090 ((4-nitroanilino)methyl)benzo[f]quinazolin-1 (2H)-one
N-(4-(((3-Amino-1,2-dihydro-1-oxobenzo[f]quinazolin-9-yl)methyl)amino)benzoyl)-L-glutamic acid
3-Amino-9-((4-nitroanilino)methyl)benzo[f]quinazolin-1 (2H)-one
9-((4-Acetylanilino)methyl)-3-aminobenzo[f]quinazolin-1(2H)-one
(RS)-2-(2-(4-(((1,2-Dihydro-3-methyl-1-oxobenzo[f]quinazolin-9-yl)methyl)amino)phenyl)-2-oxoethyl) glutaric acid
Ethyl-4-(4-(((1,2-dihydro-3-methyl-1-oxobenzo[f]quinazolin-9-yl) methyl)amino)phenyl)-4-oxobutyrate
4-(4-(((1,2-Dihydro-3-methyl-1-oxobenzo[f]quinazolin-9-yl)methyl)amino)phenyl)-4-oxobutyric acid
N-(4-(((1,2-Dihydro-3-methyl-1-oxobenzo[f]quinazolin-9-yl)methyl)amino)-2-fluorobenzoyl)glycine
Ethyl N-(4-(((1,2-Dihydro-3-methyl-1-oxobenzo[f]quinazolin-9-yl)methyl)amino)-2-fluorobenzoyl) glycinate Certain compounds of the formula (I) contain asymmetric carbon atoms and are, therefore, capable of existing as optical isomers. The individual isomers and mixtures of these are included within the scope of the present invention.

Salts of the compounds of the present invention may comprise acid addition salts derived from an amino group or anionic species derived from a compound of formula (I), for example when this is substituted by a carboxy group, and a cation. In both types of salts, the therapeutic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycollic, gluconic, succinic and methanesulphonic and arylsulphonic, for example p-toluenesulphonic, acids. Examples of salts comprising an anionic species derived from a compound of formula (I) and a cation include ammonium salts, alkali metal salts, such as sodium and potassium salts, alkaline earth salts, such as magnesium and calcium salts, and salts formed with organic bases, for example, amino salts derived from mono-, di- or tri-(lower alkyl) or (lower alkanol)amines, such as triethanolamine and diethylamino-ethylamine, and salts with heterocyclic amines such as piperidine, pyridine, piperazine and morpholine. The pharmaceutically acceptable salts together with the salts which are not thus acceptable have utility in the isolation and/or the purification of the compounds of the invention, and the pharmaceutically unacceptable salts are also useful in being convertible to the pharmaceutically acceptable salts by techniques well known in the art.

Esters of compounds of the formula (I), formed from compounds of the formula (I) which contain a carboxy group are often useful intermediates in the preparation of the parent acid.

One particularly preferred compound of the present invention is a compound, GW1843 (also called GW1843U89 or 1843U89 herein), of the formula:

GW1843

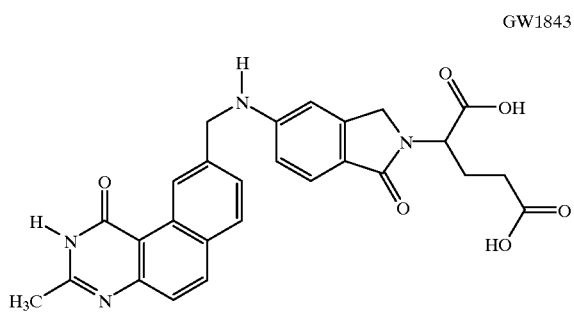

As used herein, the liposomal formulations of GW1843 are referred to as NX1843.

As used herein, the term "liposome" refers to unilamellar vesicles or multilamellar vesicles such as are described in U.S. Pat. No. 4,753,788, the contents of which are incorporated herein by reference.

"Unilamellar liposomes," also referred to as "single lamellar vesicles," are spherical vesicles comprised of one lipid bilayer membrane which defines a single closed aqueous compartment. The bilayer membrane is composed of two layers of lipids; an inner layer and an outer layer (leaflet). The outer layer of the lipid molecules are oriented with their hydrophilic head portions toward the external aqueous environment and their hydrophobic tails pointed downward toward the interior of the liposome. The inner layer of the lipid lays directly beneath the outer layer, the lipids are oriented with their heads facing the aqueous interior of the liposome and their tails toward the tails of the outer layer of lipid.

"Multilamellar liposomes," also referred to as "multilamellar vesicles" or "multiple lamellar vesicles," are composed of more than one lipid bilayer membrane, which membranes define more than one closed aqueous compartment. The membranes are concentrically arranged so that the different membranes are separated by aqueous compartments, much like an onion.

The terms "encapsulation" and "entrapped," as used herein, refer to the incorporation or association of the BTSI in or with a liposome. BTSI may be present in the interior aqueous space of the liposome, in the inner or outer leaflet of the membrane bilayer, partially buried in the outer leaflet of the bilayer and partially external to the liposome, or associated with the surface of the liposome, e.g., by electrostatic interactions, or a combination of these.

The term "excipient," as used herein, refers to a substance or substances that can facilitate the stability of drug product, including, but not limited to, the stability of pH, the stability of colloidal properties of liposome, and chemical stability of drug substance and phospholipids. Examples of excipients include, but are not limited to, the acid, sodium or ammonium forms of monovalent anions such as chloride, acetate, lactobionate and formate; divalent anions such as aspartate, succinate and sulfate; and trivalent ions such as citrate and phosphate.

"Phospholipid" refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), dioleoylphosphatidylcholine (DOPC), hydrogenated egg phosphatidylcholine (HEPC), dielaidoylphosphatidylcholine (DEPC), dipalmitoylphosphatidylcholine (DPPC) and dimyristoylphosphatidylcholine (DMPC) are suitable phosphatidylcholines for use in this invention. All of these phospholipids are commercially available. Preferred PCs are HSPC and DSPC; the most preferred is HSPC.

Further, phosphatidylglycerols (PG) and phosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Distearoylphosphatidylglycerol (DSPG) is the preferred negatively charged lipid when used in formulations. When a negatively charged lipid, such as DSPG, is included in the formulation, it is preferred that it is in a molar amount of less than 20% of the total lipid, and more preferably less than 5%. Other suitable phospholipids include phosphatidylethanolamines, phosphatidylinositols, and phosphatidic acids containing lauric, myristic, stearoyl, and palmitic acid chains. Further, incorporation of polyethylene glycol (PEG) containing phospholipids is also contemplated by the present invention.

The term "parenteral" as used herein refers to intravenous (IV), intramuscular (IM), subcutaneous (SubQ) or intraperitoneal (IP) administration.

Any phospholipid:BTSI ratio that is efficacious is contemplated by this invention. Preferred phospholipid:BTSI molar ratios are 5:1 to 75:1, more preferably 8:1 to 20:1. Preferred liposomal formulations include phospholipid:cholesterol molar ratios over the range of 5:1 to 2:1.5. The most preferred liposomal formulation is 2:1 PC:cholesterol. In the preferred embodiment, the liposomes are unilamellar vesicles having a median size less than 100 nm, wherein the phospholipid is hydrogenated soy phosphatidylcholine (HSPC) and includes cholesterol in a 2:1 molar ratio and the BTSI is GW1843.

Generally, the process of preparing the formulation embodied in the present invention is initiated with the preparation of a solution from which the liposomes are formed. This is done, for example, by weighing out a quantity of a phosphatidylcholine and cholesterol and dissolving them in an organic solvent, preferably chloroform, or a mixture of solvents, preferably chloroform and methanol. The solution is evaporated to form a solid lipid phase such as a film or a powder, for example, with a rotary evaporator, spray dryer or other means. The preferred drying method is using a spray dryer. The film or powder is then hydrated with an aqueous solution containing the active drug, and with or without excipients to form a liposome dispersion. It is preferred that no excipient is used other than acid or base used for pH adjustment of the drug solution. The lipid film or powder dispersed in the drug solution is heated to a temperature from about 25° C. to about 70° C. depending on the phospholipids used.

Multilamellar liposomes are formed by agitation of the dispersion, preferably through shaking or mixing. Unilamellar vesicles are formed by the application of energy, such as a shearing force, or cavitation, to an aqueous dispersion of the lipid solid phase, e.g., by sonication or the use of a microfluidizing apparatus, or an extrusion apparatus, or a homogenizer or a French press. Liposomes can also be prepared using either injection, freezing and thawing, dialyzing away a detergent solution from lipids, or other known methods used to prepare liposomes. The size of the liposomes can be controlled using a variety of known techniques including the duration of the application of energy. Preferably, a homogenizing apparatus is employed to form unilamellar vesicles having diameters of less than 100 nanometers at a pressure of 3,000 to 20,000 psi, preferably 10,000 to 14,000 psi and a temperature of about the aggregate transition temperature of the lipids, preferably above 55° C. for a HSPC:Chol formulation.

Unentrapped excipient and/or drug is removed from the liposome dispersion by buffer exchange to aqueous solution using either dialysis, size exclusion column chromatography (Sephadex G-50 resin) or ultrafiltration (also known as cross filtration) (50,000–300,000 molecular weight cut off).

The therapeutic use of liposomes can include the delivery of drugs which are normally toxic in the free form. In the liposomal form, the toxic drug may be directed away from the sensitive tissue where toxicity can result and targeted to selected areas where they can exert their therapeutic effects. Liposomes can also be used therapeutically to release drugs slowly, over a prolonged period of time, thereby reducing the frequency of drug administration through an enhanced pharmacokinetic profile. In addition, liposomes can provide a method for forming an aqueous dispersion of hydrophobic drugs for intravenous delivery.

The route of delivery of liposomes can also affect their distribution in the body. Passive delivery of liposomes involves the use of various routes of administration e.g., parenterally, although other effective administration forms, such as intraarticular injection, inhalant mists, orally active formulations, transdermal iotophoresis or suppositories are also envisioned. Each route produces differences in localization of the liposomes.

The invention also provides a method of inhibiting the growth of tumors, both drug resistant and drug sensitive, by delivering a therapeutic or effective amount of liposomal BTSI to a tumor, preferably in a mammal. The optimal quantity and spacing of individual dosages of the formulations herein will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses given per day for a defined number of days, can be ascertained by those skilled in the art using conventional course of treatment determination tests.

Inhibition of the growth of tumors associated with all cancers is contemplated by this invention, including multiple drug resistant cancer. Cancers for which the described liposomal formulations may be particularly useful in inhibiting are colorectal, ovarian, lung, breast, head and neck, prostate, uteran, glioblastoma, and sarcomas. In addition, it is contemplated that the formulations described and claimed herein can be used in combination with other anticancer treatments, including, but not limited to, 1) taxol (paclitaxel) and platinum complexes for treating ovarian cancer; 2) 5FU and leucovorin or levamisole for treating colorectal cancer; 3) cisplatin and etoposide for treating lung, 4) topo I inhibitors such as topotecan, irinotecan, and NX211, and 5) anthracyclines, such as doxorubicin or doxil.

This invention will be more fully understood by reference to the following examples, which are intended to be illustrative of the invention, and not limiting thereof. Example 1 describes the liposomal formulations of GW1843. Example 2 describes single dose pharmacokinetics of four liposomal formulations. Example 3 describes the comparison of plasma pharmacokinetic parameters between free GW1843 and a liposomal formulation of GW1843. Example 4 describes the comparison of two independent lots of a single NX1843 formulation. Example 5 describes the comparison of different liposome formulations and determination of the effect of animal weight on plasma pharmacokinetics. Example 6 describes plasma pharmacokinetics following a single intravenous bolus administration. Example 7 describes preclinical studies on the TS inhibitor GW1843 and the liposomal formulation NX 1843.

EXAMPLE 1

Liposomal Formulations of GW1843

Phospholipids and cholesterol used herein were obtained as dry powders from Avanti Polar Lipids, Nippon Fine Chemical, Lipoid, or Sygena and were used without further purification. All other chemicals were reagent grade and were used without further purification.

The liposome preparation of GW1843 consists of the encapsulation of the drug in the internal space of liposomes. First, lipid films or spray dried powders containing hydrogenated soy phosphatidylcholine and cholesterol were prepared. HSPC:Chol at 2:1 molar ratio was prepared using spray dry method. The lipids were dissolved in chloroform up to 20% w/w. The lipid components in the organic solvent solution was then dried down to a powder using nitrogen gas between 72–78° C. HSPC:Chol at 4:1 molar ratio was prepared using the film method. To prepare lipid films, a solvent mixture (273 mg/ml) of chloroform and methanol (1:1 volume ratio) was used to dissolve the lipid components. The solvent was then removed by running nitrogen through the solution while the solution is heated in a 65° C. temperature bath. Each lipid powder or film was hydrated at lipid concentrations in the final product up to 100–200 mg/ml in an aqueous solution containing the active drug at concentrations of 20–225 mg/ml, with or without the presence of phosphate buffer (used to buffer solution pH), in the pH range of 7–9. Samples NA-1022-63A, NA-1022-59A, GC-1007-27, and GC-1020-36 were prepared using 150 mM phosphate buffer. The other samples were prepared without phosphate buffer. (AT-1084-95B) was incubated with acetic acid at above the phase transition temperature of the phospholipid, which may have resulted in the observed low pH of the final product (Table 1A). HSPC:Cholesterol molar ratio were between 4:1 to 2:1. Small unilamellar liposomes (<100 nm, median diameter using the MicroTrac Ultrafine Particle Analyzer) were then formed from these mixtures at temperatures above the lipid phase transitions (~55° C.) using probe sonication. Drug and/or excipients that were not entrapped in the aqueous core of the liposomes were removed from the liposome dispersion generally by buffer exchange to water or 9% sucrose using size exclusion column chromatography (Sephadex G-50 resin). For preparations that use water as eluent, sucrose was added subsequent to the separation of unentrapped drug and/or excipients from liposomes.

Samples were filtered at ambient temperature through a 0.22 micron filter composed of either cellulose acetate or polyether sulfone. Results of characterization are shown below in Table 1A.

Other formulations were prepared using phospholipids other than HSPC (Table 1B). A negatively charged phosphatidylcholine, DSPG, was also used in one formulation (Table 1B). Lipid films were prepared as described above for AL1230-058, AL1230-052, AL1230-048, and AL1230-055 with 100 mg/ml chloroform and methanol. Spray dried powders were prepared as described above for AL1230-041. Each lipid film or powder was hydrated in a drug solution of 100 mg/mL, pH 7.5. After mixing, the hydrated lipid was homogenized using a homogenizer (Panda made by Niro) at ~65° C. and ~13,000 psi pressure to form small unilamellar vesicles. After homogenization, the liposomes were cross-filtered against water for injection to remove the unencapsulated drug. At the end of cross-filtration, sucrose was added to the bulk to a concentration of approximately 9%. The liposome solutions were filtered through 0.2 μm Polyether sulfone (PES) filter. Test results of these formulations are shown in Table 1B.

Additional formulations were prepared using different excipients, such as sucrose, phosphate, citrate, and succinate, for the HSPC:Chol (molar ratio 2:1) formulation. The spray dried powder of HSPC:Chol (2:1) molar ratio) was hydrated in a drug solution of 100 mg/ml, pH 7.5. After mixing, the hydrated lipid was homogenized using a homogenizer (Panda made by Niro) at 65° C. and 13,000 psi pressure to form small unilamellar vesicles. After homogenization, the liposomes were cross-filtered against water for injection to remove the unencapsulated drug. At the end of cross-filtration, sucrose was added to the bulk to a concentration of approximately 9%. Additional buffer excipients were added (Table 1C) to a desired concentration and solution pH was adjusted. The liposome solutions were filtered through 0.2 μm Polyether sulfone (PES) filter. Some test results of these formulations are presented in Table 1C. The stability data of the formulations are listed in Table 1D. The formulations are stable over at least one month at 2–8° C.

EXAMPLE 2

Single Dose Pharmacokinetics of Four Liposomal Formulations

The plasma pharmacokinetics of free GW1843 and 4 different liposome formulations (see Table 1A; GC-1007-27, GC-1020-36, NA-1022-63A, and NA-1022-59A) of GW1843 in rats following a single intravenous bolus administration are compared. The liposome formulations differed by the pH utilized to load the liposome. NX1843 lot nos. GC-1007-27, GC-1020-36, NA-1022-63A, and NA-1022-59A were loaded at pH 7.0, 7.4, 7.3 and 7.5, respectively.

Materials and Methods

A total of fifteen Sprague Dawley rats were used in the study. Each rat weighed approximately 250 grams. Three animals were assigned to each group (five groups in total). Individual animals were weighed and dosed at 1 mg/kg body weight by intravenous bolus administration into the tail vein while under isoflurene anesthesia. EDTA blood samples were taken at the time points shown in Table 2 while under isoflurene anesthesia and immediately processed into plasma. Plasma was stored at −20° C. until analysis.

Plasma samples were prepared and analyzed for GW1843 by the use of a non-validated HPLC assay. Following methanol precipitation of plasma protein, the soluble GW1843 was separated by C-18 reverse phase column chromatography. Separation was achieved by an isocratic method. Running buffer consisted of 80% acetonitrile and 20% 100 mM ammonium acetate pH=5.3. Area under the peak versus concentration of GW1843 was used to construct the standard curve.

Pharmacokinetic parameters were determined by non-compartmental analysis (WinNonlin version 1.5). Pharmacokinetic parameters were determined for each experimental group using the average concentration versus time values for each group. The following parameters were calculated: Maximum plasma concentration (Cmax); area under the plasma concentration versus time curve extrapolating to infinite time (AUCinf) or to last time point (AUClast); elimation half-life (Elim.T½); mean residence time (MRT) plasma clearance (Cl) and volume of distribution at steady state (Vss).

Results

The plasma concentrations for each dose group are summarized in Table 2. Calculated pharmacokinetic parameters are shown in Table 3.

Noncompartmental Analysis

Noncompartmental analysis makes no assumptions about the underlying pharmacokinetic model. Estimates for the maximum achieved concentrations (Cmax) in the plasma ranged from 15.5 to 24.8 μg/mL for the liposomal formulations and 1.3 μg/mL for the free drug. The estimated elimination half-life (Elim.t½) of all four liposome formulations was significantly greater than for the free drug. The elimination half-lives of the liposome formulations were all approximately 18.5 hours while the free drug displayed an elimination half-life of approximately 0.5 hours. The area under the plasma concentration versus time curve (AUCinf) for the liposomal formulations ranged from 266,740 to 462,920 (h×ng/mL) compared to just 263 (h×ng/mL) for the free drug. This latter result is reflected in the plasma clearance, which ranged from 2.16 to 3.75 mL/h for the liposome formulations and was 3,805 mL/h for the free drug.

Finally, the volume of distribution at steady state (Vss) for the liposome formulations ranged from 2 to 3 times the expected plasma volume of the rat (31.2 mL/kg) (3) while the free drug had a volume of distribution 18 to 30-fold greater than the liposome formulations.

EXAMPLE 3

Comparison of Plasma Pharmacokinetic Parameters Between Free GW1843 and a Liposomal Formulation of GW1843

Materials and Methods

GW1843 (M.W. 500.51 g/mol) was obtained from Glaxo Wellcome, Inc. and suspended as an aqueous. Briefly, 616.74 milligrams of GW1843 was suspended in 1.4 mL 2 N NaOH. The solution was mixed until dissolved. To the dissolved solution 30 mL saline was added. The pH was adjusted to 7.15 with 2 N HCl. Finally, the solution was brought to 46.545 mL with saline. The nominal concentration was 13.25 mg/mL. UV absorption in 0.1 N sodium hydroxide at 266 nm, based on an extinction coefficient of $4.34 \times 10^4$ cm$^{-1}$ M$^{-1}$, determined the concentration. The concentration by UV spectroscopy was 13.97 mg/mL (5.4% difference from expected). The value determined by spectroscopy was utilized for standards in the HPLC assay. NX1843 lot SMC-991-96 (see Table 1A) was used for making quality control solutions.

Male Sprague-Dawley rats weighing 343.91 to 420.19 grams were used for the study. The in-life phase of the study was conducted in Boulder Colo. in accordance with the guidelines for animal welfare and care (NRC Publication Guide for the Care and Use of Laboratory Animals, 1996). IACUC protocol number N98010. Animals were allowed free access to food and water before and during treatment.

Individual animals treated with NX1843 were weighed and dosed at 1 mg/kg body weight by intravenous bolus administration into the tail vein while under isoflurane anesthesia.

Serial EDTA-blood samples (0.5 mL) were obtained at 5, 15, 30 and 45 minutes, and 1, 1.5 and 2 hr post-dosing for the GW1843 group while animals were under isoflurane anesthesia. For the NX1843 group, serial EDTA-blood samples (0.5 mL) were obtained at 10, 30 and 90 minutes and 4, 8, 24, 32, 48, 72 and 96 hours post-dosing. The EDTA-blood samples were immediately processed for plasma and plasma samples were stored at −20° C. until analysis.

An isocratic reverse phase high performance liquid chromatographic (HPLC) procedure was used for rapid determination of the total GW1843 concentration in rat EDTA-plasma. Following methanol precipitation of plasma protein (2 parts methanol to 1 part plasma), the protein was removed by centrifugation at 14,000×g for 10 minutes. A ZORBAX Eclipse™ XBD-C18 column (3 mm×15 cm) configured with a guard column was used to separate the soluble GW1843 (injection volume 20 μL). The HPLC buffer consisted of 80% 100-mM ammonium acetate pH 5.3, and 20% acetonitrile and the flow rate was 0.4 mL/min. The total run time was seven minutes and GW1843 was detected and quantified by ultraviolet absorbance at 264 nm. The standard curve consisted of free GW1843 spiked rat EDTA-plasma while the quality control samples consisted of NX1843 spiked rat EDTA-plasma. The range of the standard curve was 0.1 to 30.0 μg/mL.

The pharmacokinetic parameters for total GW1843 after i.v administration of GW1843 or liposome encapsulated GW1843 were assessed by a non-compartmental method using WinNonlin (version 1.5). The log/linear trapazoidal rule was used. For non-compartmental analysis, all three time points were utilized for the estimation the elimination phase for free GW1843 while the last 5 time points were utilized to estimate the elimination half-life of NX1843. Cmax values were estimated by extrapolation to zero time. Pharmacokinetic parameters were determined for each animal in the study. From values obtained in each group the mean and SD of each parameter was determined. The parameters estimated included:

| | |
|---|---|
| Cmax | The maximum plasma concentration. |
| AUC(0-last) | The area under the plasma concentration versus time curve up to the last time plasma time point measured. |
| ke | The slope of the terminal elimination phase, estimated by linear regression. |
| t½ | The half-life of the terminal elimination phase (0.693/ke). |
| MRT(0-inf) | Mean residence time extrapolated to infinity. |
| AUC(0-inf) | The area under the concentration versus time curve extrapolated to infinity. |

The observed clearance (CL) of GW1843 following administration was calculated as:

$$CL = Dose_{iv}/AUC$$

Comparison of treatment groups was performed by unpaired t-tests of data obtained in the same experiment. A p-value of <0.05 was considered significant. Tests were performed using GraphPad Instat version 1.0 (GraphPad Software).

Results

Non-Compartmental Analysis of GW1843 and Liposome Encapsulated GW1843 (NX1843)

The total plasma concentrations for the GW1843 dose group are summarized in Table 4 while the corresponding total plasma concentrations for the liposome encapsulated GW1843 (NX1843; SMC-991-96) dose group are summarized in Table 5. The estimated values of several calculated pharmacokinetic parameters for GW1843 and NX1843 are given in Table 6 and Table 7, respectively. Pharmacokinetic values for the GW1843 dose group are based on a terminal half-life estimated by all three measured GW1843 plasma concentrations. This probably results in an underestimate of the half-life and thus a slight underestimate of the AUC. However, such an approach is necessitated by the limited data at this dose level.

FIG. 1 shows the log concentration versus time curves for the two dose groups.

Estimates for the maximum achieved concentrations (Cmax) in the plasma of animals receiving NX1843 ranged from 22.1 to 28.7 μg/mL of total GW1843. These values were significantly greater than observed for free GW1843 (Range 1.62 to 1.99 μg/ml). The estimated (mean±SD) terminal half-life (Elim.t½) of the liposome formulation was 16.6±0.86 hours while the free drug displayed an elimination half-life of 0.142±0.007 hours. The area under the GW1843 plasma concentration versus time curve [AUC (0–inf)] for the liposomal formulation was 524±55.9 hr. μg/mL compared to just 0.27±0.028 hr. μg/mL for the free drug. This latter result is reflected in the plasma clearance, which was 1.93±0.206 mL/hr for the liposome formulation and was 3,740±456 mL/hr for the free drug. Finally, the volume of distribution at steady state (Vss) for the liposome formulation was less than twice the expected plasma volume of the rat (31.2 mL/kg) (3) while the free drug had a volume of distribution on the order of 14.6-fold greater than the liposome formulation.

Liposome encapsulation of GW1843 gave an approximately 1,940-fold increase in total plasma exposure in comparison to the free drug. This value is similar to the values obtained in Example 2 where 1,000 to 1,760-fold increases were observed.

In general, the pharmacokinetic parameters of NX1843 observed in this Example were similar to those observed in Example 2.

The average terminal half-life of 18.0 hours determined for the NX1843 formulation in this example was not significantly different from any of the terminal half-lives (Range 17.7 to 20.2 hours) obtained for the four NX1843 formulations tested in Example 2.

EXAMPLE 4

Comparison of Two Independent Lots of a Single NX1843 Formulation

NX1843 lot numbers SMC-991-96 and SMC-1092-09 (see Table 1A) were used.

Male Sprague-Dawley rats weighing 207.16 to 219.27 grams were used for the study. The in-life phase of the study was conducted in Boulder Colo. in accordance with the guidelines for animal welfare and care (NRC Publication Guide for the Care and Use of Laboratory Animals, 1996). IACUC protocol number N98010. Animals were allowed free access to food and water before and during treatment.

Individual animals were weighed and dosed at 1 mg/kg body weight by intravenous bolus administration into the tail vein while under isoflurane anesthesia.

Serial EDTA-blood samples (0.5 mL) were obtained at 10, 30 and 90 minutes and 4, 8, 24, 32, 48, 72 and 96 hours post-dosing (nominal times) while under isoflurane anesthesia. The EDTA-blood samples were immediately processed for plasma and stored at $-20°$ C. until analysis.

The total concentration of GW1843 in plasma was determined as in Example 3.

The pharmacokinetic parameters for total GW1843 after intravenous administration of liposome encapsulated GW1843 were assessed as described in Example 3.

Comparison of treatment groups was performed by unpaired t-tests of the data. A p-value of <0.05 was considered significant except when multiple comparisons were performed in which case the Bonferroni correction was utilized. Tests were performed using GraphPad Instat version 1.0 (GraphPad Software).

Results

The plasma concentrations for liposome encapsulated GW1843 (NX1843) lot SMC-1092-09 dose group are summarized in Table 8 while the corresponding plasma concentrations for the NX1843 lot SMC-991-96 dose group are summarized in Table 9. The estimated values of several calculated pharmacokinetic parameters for NX1843 lot SMC-1092-09 and NX1843 lot SMC-991-96 are given in Table 10 and Table 11, respectively.

Estimates for the maximum achieved concentrations (Cmax) in the plasma of animals receiving NX1843 lot SMC-1092-09 ranged from 16.9 to 23.1 µg/ml of total GW1843 (mean=19.1 µg/mL). Estimates for the Cmax in the plasma of animals receiving NX1843 lot SMC-991-96 ranged from 15.0 to 18.4 µg/mL of total GW1843 (mean= 16.8 µg/mL). The observed differences in the mean Cmax values for each group were not significantly different (p=0.2161). The estimated (mean±SD) terminal half-life (Elim.t½) obtained for lot SMC-1092-09 and lot SMC-991-96 were 12.2±0.06 hr and 11.7±0.96 hours, respectively. The observed differences in the half-lives obtained for the two lots were not significantly different (p=0.3386). Likewise, the differences observed for the mean of the Vss for lot SMC-1092-09 (70.8 mL/kg) and lot SMC-1092-991-96 (65.8 mL/kg) were not significant (p=0.2784). Finally, the observed differences between the AUC(0–inf) of the two lots [276±21.9 µg.hr/mL for SMC-1092-09 and 293±53.8 µg.hr/mL for SMC-991-96 (p=0.5797)] or between the clearance of the two lots [3.65±0.28 mL/hr.kg for SMC-1092-09 and 3.50±0.59 mL/hr.kg for SMC-991-96 (p=0.6623)] were not significant.

Several pharmacokinetic parameters obtained for lot SMC-991-96 in this Example were significantly different from those obtained for this same lot in Example 3. Both Examples utilized the same dose, route of administration and strain of rats (see Example 3). Two-tailed, unpaired t-tests were used to test the statistical significance of five different pharmacokinetic parameters. Because five comparisons were performed a Bonferroni correction was made such that a value of p<0.01 was necessary for significance.

The differences observed in the means were statistically significant for all five parameters tested. Statistically significant differences were observed for plasma clearance (p=0.0024), volume of distribution at steady state (p=0.0027), plasma terminal half-life (p=0.0003), Cmax (p=0.0022) and AUC(0–inf) (p=0.0010).

The AUC(0–inf) for this Example was 55% of the AUC (0–inf) achieved in Example 3. Examination of the AUC over the first 24 hours [AUC(0–24)] shows that lot SMC-991-96 in this Example (206±29.4 µg.hr/mL) was only 64% of the AUC(0–24) achieved for the same lot in Example 3 (320±27.5 µg.hr/mL). This data revealed that the majority of the difference in plasma exposure was observed in the first 24 hours. However, the AUC(0–24) was 61% of the AUC (0–inf) in Example 3, while it was 70% in this study suggesting that the faster terminal phase seen in this study also played a role in reducing the overall plasma exposure.

No statistically significant pharmacokinetic differences were observed between lots SMC-1092-09 and SMC-991-96.

Statistically significant pharmacokinetic differences were observed between the results in this Example and Example 3 for lot SMC-991-96.

Differences in animal weight between this Example and Example 3 likely have contributed to the pharmacokinetic differences observed between studies for lot SMC-991-96.

EXAMPLE 5

Comparison of Different Liposome Formulations and Determination of the Effect of Animal Weight on Plasma Pharmacokinetics Materials and Methods NX1843 lot numbers SMC-1092-09, AT-1084-97B, AT-1084-91B and AT-1084-88B were used.

Male Sprague-Dawley rats weighing 207.78 to 228.76 grams were used to evaluate all lots. In addition, large male Sprague-Dawley rats weighing 403.12 to 418.28 grams were used to evaluate lot AT-1084-91B in large rats. The in-life phase of the study was conducted in Boulder Colo. in accordance with the guidelines for animal welfare and care (NRC Publication Guide for the Care and Use of Laboratory Animals, 1996). IACUC protocol number N98010. Animals were allowed free access to food and water before and during treatment.

Individual animals were weighed and dosed at 1 mg/kg body weight by intravenous bolus administration into the tail vein.

Serial EDTA-blood samples (0.5 mL) were obtained at 10, 30 and 90 minutes and 4, 8, 24, 32, 48, 72 and 96 hours post-dosing. The EDTA-blood samples were immediately processed for plasma and stored at −20° C. until analysis. Plasma samples were obtained under isofluorane anesthesia.

The total concentration of GW1843 in plasma was determined as in Example 3.

The pharmacokinetic parameters for total GW1843 after intravenous administration of GW1843 or liposome encapsulated GW1843 were assessed as described in Example 3.

Statistical testing was performed by a one way ANOVA for unpaired data. A p-value of <0.05 was considered significant. Tests were performed using GraphPad Instat version 1.0 (GraphPad Software).

Results

Animals were assigned to one of five groups (n=4 in each group). Groups A–D were composed of animals with an average weight of 223 grams while Group E was composed of animals with an average weight of 409 grams. Animals in each group received a 1 mg/kg i.v. bolus dose of a liposome encapsulated GW18343 formulation. Group A was dosed with lot AT-1084-97B, a formulation containing a basic internal pH. Groups B, C and E each received the standard NX1843 formulation. Group B received test article from lot SMC-1092-09 while groups C and E received the test article from lot AT-1084-91B. Group D animals were dosed with lot AT-1084-88B, a lot consisting of a high lipid to drug ratio. The total plasma GW1843 concentrations for each animal in each dose group are shown in Tables 12–16. The estimated values of several calculated pharmacokinetic parameters determined by non-compartmental analysis for each animal in each dose group are shown in Tables 17–21. A one way ANOVA was performed on the clearance [Dose($\mu$g/kg)/AUC(0–inf) ($\mu$g.hr/mL)] of all five groups. This test revealed significant differences between groups (p<0.0001). Seven post tests were performed (between groups A and B, A and C, B and C, B and D, B and E, C and D, and C and E) the results of which are discussed below.

Intra-Study Analysis of the Pharmacokinetic Parameters of Two Independent Lots of the Same NX1843 Formulation Two independent lots of the same standard liposome formulation of NX1843 were compared in equivalent sized (~220 gram) rats. Group B animals received lot SMC-1092-09 while group C animals received lot AT-1084-91B. The plasma terminal half-life obtained for group B (10.6±1.10 hr) was not obviously different from the terminal half-life obtained for group C (11.7±0.535 hr). Although the AUC (0–inf) obtained for group B (253±28.4 $\mu$g.hr/mL) appeared to be less than the AUC(0–inf) obtained for group C (347±51.2 $\mu$g.hr/mL), post tests following the one way ANOVA analysis for clearance showed no statistically significant differences in clearance between group B and group C (p=0.0606).

Although this plasma clearance result may also be viewed as "marginally significant," a similar intra-study comparison of independent lots of the same liposome encapsulated formulation of GW1843 (NX1843) gave unequivocal results (Example 4). In this study, one group of male Sprague-Dawley rats received 1 mg/kg of lot SMC-1092-09 while the other group of male Sprague-Dawley rats received 1 mg/kg of lot SMC-991-96. This study did not show statistically significant differences between the two groups in any plasma pharmacokinetic parameter analyzed including plasma clearance (p=0.6623).

Table 22 summarizes the total GW1843 plasma pharmacokinetic parameters obtained from two studies for three independent lots of the standard formulation of NX1843 (Examples 4 and 5). All of this data has been determined from male Sprague-Dawley rats of equivalent weight following a 1 mg/kg i.v. bolus dose of test article. In light of the data as a whole, no inter-lot differences in total GW1843 plasma pharmacokinetic parameters have been observed between different lots of the same liposome formulation.

Inter-Study Analysis of the Pharmacokinetic Parameters Obtained from Two Studies with the Same Lot of the Standard Liposome Formulation of GW1843 (NX1843) in Rats of Equivalent Weight In this Example, rats (group B) received a 1 mg/kg i.v. bolus dose of lot SMC-1092-09. In Example 4, a group of rats of similar weight also received a 1 mg/kg i.v. bolus dose of lot SMC-1092-09. The total GW1843 plasma pharmacokinetic parameters obtained for the rats that received this lot of test article in this Example and in Example 4 (study R990198-138E) are shown in Table 22. No obvious differences between the studies can be detected. The plasma terminal half-life obtained for group B in this Example (study R2000007-138E) (10.6±1.10 hr) was not obviously different from the terminal half-life obtained for the SMC-1092-09 group in Example 4 (study R990198-138E) (12.2±0.06 hr). Likewise, the plasma clearance obtained for group B in this Example (3.99±0.417 mL/hr.kg) was not obviously different from the plasma clearance obtained for the SMC-1092-09 group in Example 4 (study R990198-138E) (3.65±0.283 mL/hr.kg).

High Internal pH and High Lipid to Drug Ratio Formulations

The pharmacokinetic profiles of two alternative liposome GW1843 formulations were examined in approximately 220-gram animals. Group A received a formulation containing a high internal pH while group D received a formulation containing an increased lipid to drug ratio. For comparison, groups B and C, also composed of ~220-gram animals, received two independent lots of the standard liposome formulation of GW1843 (NX1843).

There were no obvious differences between the plasma pharmacokinetic parameters observed for the high internal pH group and the two groups that received the standard formulation. Of note, is that the terminal half-life for group A (9.83±0.215 hr) was not obviously different from the terminal half-lives observed for group B (10.6±1.10 hr) or group C (11.7±0.535 hr). Likewise, the AUC(0–inf) obtained for group A (283±23.7 $\mu$g.hr/mL) was in between the AUC(0–inf) obtained for group B (253±28.4 $\mu$g.hr/mL) and Group C (347±51.2 $\mu$g.hr/mL). Post tests following the one way ANOVA analysis for clearance, showed no statistically significant differences in clearance between group A (3.56±0.295 mL/hr.kg) and group B (3.50±0.589 mL/hr.kg) or between group A and group C (2.94±0.489 mL/hr.kg).

There were obvious differences between the plasma pharmacokinetic parameters observed for the high lipid to drug ratio group (group D) and the two groups that received the standard formulation (groups B and C). Of note, is that the terminal half-life for group D (11.7±1.88 hr) was not obviously different from the terminal half-lives observed for group B (10.6±1.10 hr) or group C (11.7 ±0.535 hr). However, the AUC(0–inf) obtained for group D (169±28.8 μg.hr/mL) appeared to be smaller than the AUC(0–inf) obtained for group B (253±28.4 μg.hr/mL) or for Group C (34 ±51.2 μg.hr/mL). Post tests following the one way ANOVA analysis for clearance showed statistically significant differences in between group D and group B (p=0.0038) and between group D and group C (p=0.0005).

NX1843 Pharmacokinetics in Large Versus Small Rats

Examination of previous pharmacokinetic studies (Example 2, 3, and Example 4) in male Sprague-Dawley rats revealed that, following a 1 mg/kg i.v. bolus dose of liposome encapsulated GW1843 (NX1843), total GW1843 plasma clearance (mL/hr.kg) may vary with animal weight. In order to test this hypothesis, two groups of male Sprague-Dawley rats in this study received a 1 mg/kg i.v. bolus dose of the same lot of NX1843 (Groups C and E). Animal weights differed between groups so that those in group C averaged 226 grams while those in group E averaged 409 grams. Examination of the resulting pharmacokinetic parameters revealed probable differences. For example, the plasma terminal half-life of group E animals was longer (14.0±2.03 hr) than for group C animals (11.7±0.535 hr). Likewise, the Cmax of group E animals was larger (25.2±1.33 μg/mL) than for group C animals (20.4±1.23 μg/mL). These differences are also reflected in differences in the AUC(0–inf) between groups C and E. Group E animals had a AUC(0–inf) of 549±58.0 μg.hr/mL while group C animals had a AUC(0–inf) of 347±51.2 μg.hr/mL. However, the one way ANOVA analysis for clearance between groups C and E showed only a "marginally significant" result (p=0.0522). When combined, though, with results from previous Examples (study numbers R990164-138E and R990198-138E) the differences between large and small animals become clear. Table 23 shows the combined results of the plasma pharmacokinetic parameters obtained from two independent lots of the same formulation of NX1843 that were studied in both large and small rats. The two experiments in large animals had similar clearance values, 1.93±0.207 mL/hr.kg and 1.84±0.191 mL/hr.kg. However, in smaller animals, higher clearance values were obtained in the two independent experiments (3.50±0.589 mL/hr.kg and 2.94±0.489 mL/hr.kg). Thus from the combined data, it is clear that values for clearance differ when determined by a μg/kg basis. If the clearance is determined, however, using total dose (mL/hr) then the clearance values obtained are similar for large and small animals. Recalculation of the clearance values shown in Table 23 by the total dose method gives 0.73 mL/hr and 0.65 mL/hr for the two studies composed of approximately 220 gram animals and gives 0.75 mL/hr and 0.74 mL/hr for the two studies composed of approximately 400 gram animals.

In equivalent sized animals, no statistically significant differences were observed between the plasma clearance (mL/hr.kg) of the liposome encapsulated GW1843 formulation (lot SMC-1092-09) obtained in the present Example and in Example 4.

In equivalent sized animals, no statistically significant differences in plasma clearance (mL/hr.kg) were observed between two independent lots (SMC-1092-09 and AT-1084-91B) of the same liposome encapsulation GW1843 formulation (NX1843).

Differences in plasma clearance (mL/hr.kg) for the standard formulation are observed based on animal weight. This conclusion is based upon comparisons of lot AT-1084-91B in large and small animals in this example and of lot SMC-1092-09 in small animals in this example and Example 4 and of lot SMC-996-91 in small animals in Example 4 and large animals in Example 3. Thus, the hypothesis given in Example 4 to explain the PK differences has been verified.

Plasma clearance appears constant between large and small rats when calculated as [Total Dose (μg)/AUC(0–inf) (μg.hr/mL)]=mL/hr.

In equivalent sized animals, the high lipid to drug ratio formulation (lot AT-1084-88B) was cleared more rapidly than was the standard formulation (lots SMC-1092-09 and AT-1084-91B) or the high internal pH formulation (lot AT-1084-97B), but was still cleared from plasma significantly more slowly than free GW1843 (Examples 2 and 3).

In equivalent sized animals, the high internal pH formulation (lot AT-1084-97B) had a plasma clearance value that was similar to the standard formulation (lots SMC-1092-09 and AT-1084-91B). Thus, this formulation was also cleared from plasma significantly more slowly than free GW1843 (Examples 2 and 3).

EXAMPLE 6

Plasma Pharmacokinetics Following a Single Intravenous Bolus Administration

The purpose of this example was to extend the analysis of alternative formulations of liposome encapsulated GW1843. Here a formulation consisting of a 4:1 HSPC to cholesterol molar ratio was tested. Other formulations consisted of a 2:1 molar ratio. Cholesterol is known to stabilize the liposome structure so that it is expected that an increased HSPC to cholesterol ratio should increase plasma clearance.

Results

NX1843 lot number AT-1105-32 (Table 1A) was used.

Male Sprague-Dawley rats weighing 244.57 to 257.19 grams were used for the study. The in-life phase of the study was conducted in Boulder, Colo. in accordance with the guidelines for animal welfare and care (NRC Publication Guide for the Care and Use of Laboratory Animals, 1996). Animals were allowed free access to food and water before and during the study.

Individual animals were weighed and dosed at 1 mg/kg body weight by intravenous bolus administration into the tail vein.

EDTA-blood samples (0.5 mL) were obtained at 10, 30 and 90 minutes and 4, 8, 24, 32, 48, and 72 hours postdosing. Samples were taken while the animals were under anesthesia (isoflurane) and the EDTA-blood samples were immediately processed for plasma and plasma samples were stored at −20° C. until analysis.

The total concentration of GW1843 in plasma was determined as in Example 3.

The pharmacokinetic parameters for total GW1843 after i.v administration of liposome encapsulated GW1843 were assessed as described in Example 3.

Comparison of treatment groups was performed by unpaired t-tests of data obtained in the same experiment. A p-value of <0.05 was considered significant. Tests were performed using GraphPad Instat version 1.0 (GraphPad Software).

Results

The total GW1843 plasma concentrations for each animal are summarized in Table 24. The estimated values of several calculated pharmacokinetic parameters for the liposome encapsulated GW1843 (NX1843) 4:1 HSPC to cholesterol molar ratio formulation are given in Table 25.

Estimates for the maximum achieved concentrations (Cmax) for total GW1843 in the plasma ranged from 14.4 µg/mL (rat #2) to 17.2 µg/mL (rat #3). The mean Cmax for all four animals was 15.8 µg/mL. The estimated (mean±SD) terminal half-life (Elim.t½) was 9.92±1.98 hours well within the range observed for the standard liposome encapsulated GW1843 formulation. The area under the total GW1843 plasma concentration versus time curve [AUC(0–inf)] was 213±22.8 hr.µg/mL. This area under the curve is somewhat less than that observed for the standard liposome formulation, range 251 to 342 hr. µg/mL This is reflected in the plasma clearance value obtained for the 4:1 HSPC to cholesterol formulation (4.74±0.472 mL/(hr.kg)). The range of mean clearance values obtained for three different lots of the standard formulation in 4 experiments with nearly equivalent sized animals (Examples 4 and 5) was 3.50 to 3.99 mL(hr.kg).

Previous studies have shown that plasma clearance, on a mL(hr.kg) basis, decreases with increasing animal weight (Example 5). The average weight of animals in this study was 250 grams while the comparative studies of the standard liposome encapsulated GW1843 formulation were performed with rats that weighed on average 220 grams (range mean weights of animals for the four studies was 215 to 224 grams). Thus, the use of animals in this study with a weight of approximately 220 grams would have likely increased the observed differences.

The NX1843 formulation consisting of a 4:1 lipid to cholesterol ratio (lot AT-1105-32) was cleared from plasma slightly faster than the standard liposome formulation. Clearance for lot AT-1105-32 was 4.74±0.472 mL(hr.kg). The range of mean clearance values obtained in nearly equivalent sized animals for three different lots of the standard formulation in 4 experiments (Examples 4 and 5) was 3.50 to 3.99 mL(hr.kg). This formulation (lot AT-1105-32) was still cleared from plasma significantly more slowly than free GW1843 (see Examples 2 and 3).

EXAMPLE 7

Preclinical Studies on the TS Inhibitor GW1843U89 and the Liposomal Formulation NX 1843

Methods

Female Nu/Nu mice (18–24 g, 10–14 weeks old) were obtained from Harlan Sprague Dawley, and housed in microisolator filtration racks and maintained with filtered acidified water and sterile lab chow ad libitum. The human colon tumor xenograft model (HCT-8, thymidine kinase (TK)−/−) was obtained from Dr. Youcef M. Rustum (Roswell Park, Buffalo, N.Y.), and established in-house as a useful model for evaluation of thymidylate synthase inhibitors. Animals were allowed to acclimate to their new environment for 1 week prior to tumor cell implantation. Tumors were established by injecting harvested tumor cells in a single subcutaneous site on the flank of the mice in the axillary region. The tumors were grown until approximately 200+/−50 mm$^3$ in size. The animals were then sorted according to body weight, grouped four animals/cage, and tattooed on the tail for permanent identification. Groups consisting of 8 tumor-bearing mice each were administered weekly doses of experimental agents by IV bolus injection through the tail vein. Tumor volumes were determined with vernier caliper measurements taken at right angles using the formula, (L×W$^2$/2) and body weights, were collected twice weekly. Data was plotted as % change in body weight vs. time in days, and % tumor volume increase vs. days.

Methods of calculating anti-tumor activity from experimental results were as follows:
Inhibition and Regression Calculations Commonly Used For Assessing Experimental Data:

$$\% \ T/C = 100 \times 1 - (T/C)$$

T=(mean) time in days for treated group to reach cutoff size (2 grams)

C=(mean) time in days for control group to reach cutoff size (2 grams)

% T/C value less than 10% is indicative of significant activity; and

% T/C value of <or=20% is indicative of moderate activity.

% Tumor Growth Inhibition $$\% \ TGI = 100 \ (W_c - W_t)/W_c = 100 \ (1 - W_t/W_c)$$

$W_C$ is the mean tumor weight of control group at time x $W_t$ is mean tumor weight of treated group at time x If the starting tumor size between groups is great, the relative differences (RW) in tumor growth of the control and treated groups is used to correct for the initial differences.

$RW = W_i/W_o$, where $W_i$ is the mean tumor weight at time x, and $W_o$ is the initial mean tumor weight.

% Regression=100 $(W_o - W_i)/W_o$; where $W_o$ is the mean tumor weight for treated group at the initiation of treatment and $W_i$=the mean tumor weight for that group at time some time x after treatment. Many times the time x=24–48 hr after the final dose of therapy.

Growth delay measures used to assess experimental results:
Tumor Cell Kill Calculations for sc Growing Tumors:

$$\text{The } \log_{10} \text{ cell kill (gross)} = [T-C \text{ value in days}/(3.32)(T_d)]$$

Where T−C=time difference in days between Treated and Control tumors to reach a defined end point; and Td is the Tumor Volume Doubling time in days from the best-fit straight line from a log-linear growth plot of the control tumors exponential growth (100–800 mg range). The conversion of the T−C values to the net log$_{10}$ tumor cell kill are provided by subtraction of the duration of the treatment period from the T−C value and then dividing by 3.32×T$_d$.

HCT-8, TK−/−xenograft Model

The initial experiment, designated NMX-427, tested the effects of GW1843U89 at two different dose levels, 50 and 100 mg/kg/day×17 days. The control group received vehicle alone. The experiment demonstrated little difference between the two dose groups, and both drug groups were significantly different from control with log cell kill values of 3.0 and 3.3 for the 50 and 100 mg/kg groups, respectively. There were two durable cures, one in each of the dose groups, which remained until termination of the experiment at day 57. The side-effect toxicity as measured by gross body weight loss was minimal in both drug-treated groups, and was greatest in the control group. This may reflect tumor induced cachexia, an effect induced by some actively growing tumors.

Figure 2:
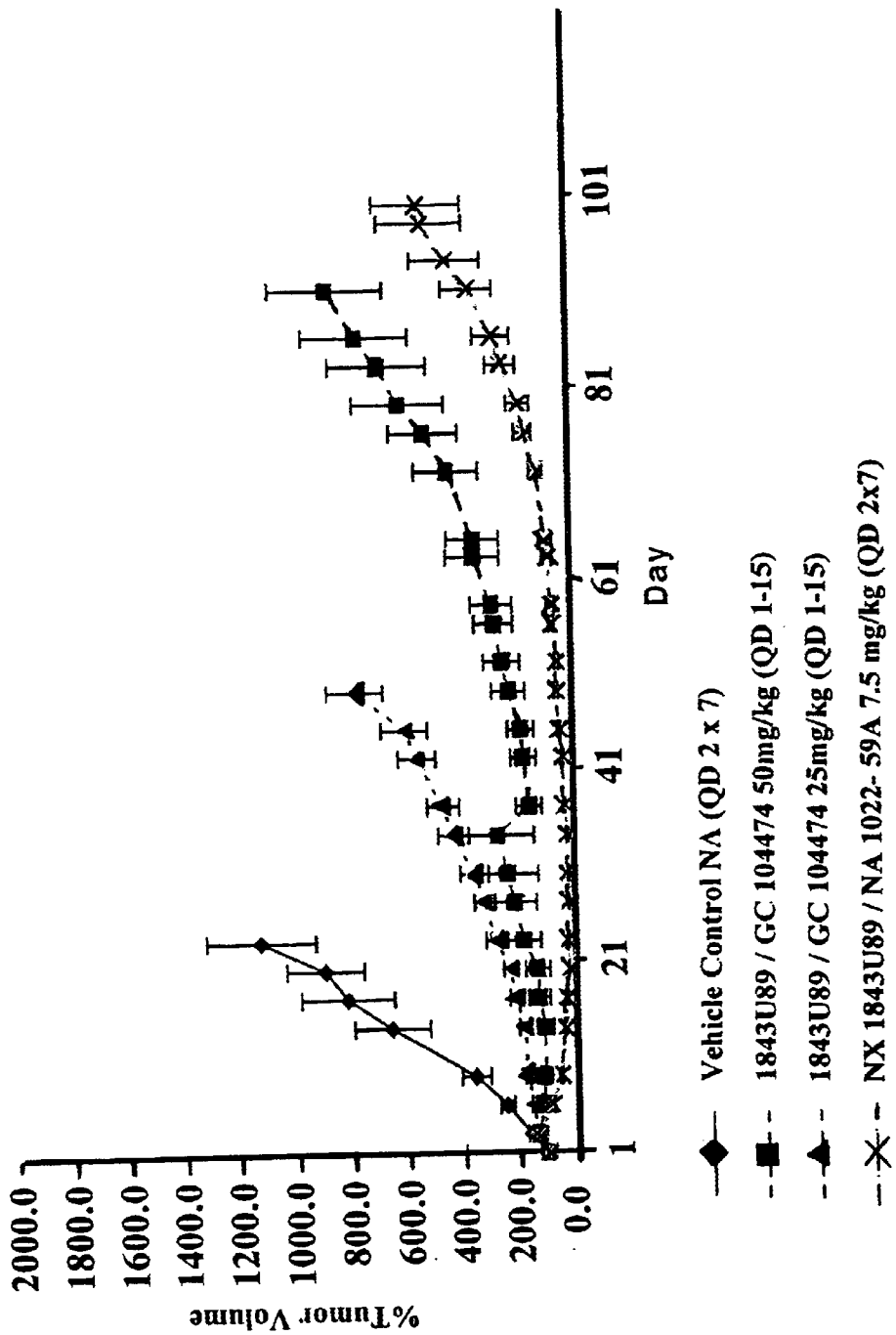
FIG. 2 depicts the tumor growth curve of HCT-8 treated tumors.
Figure 3:
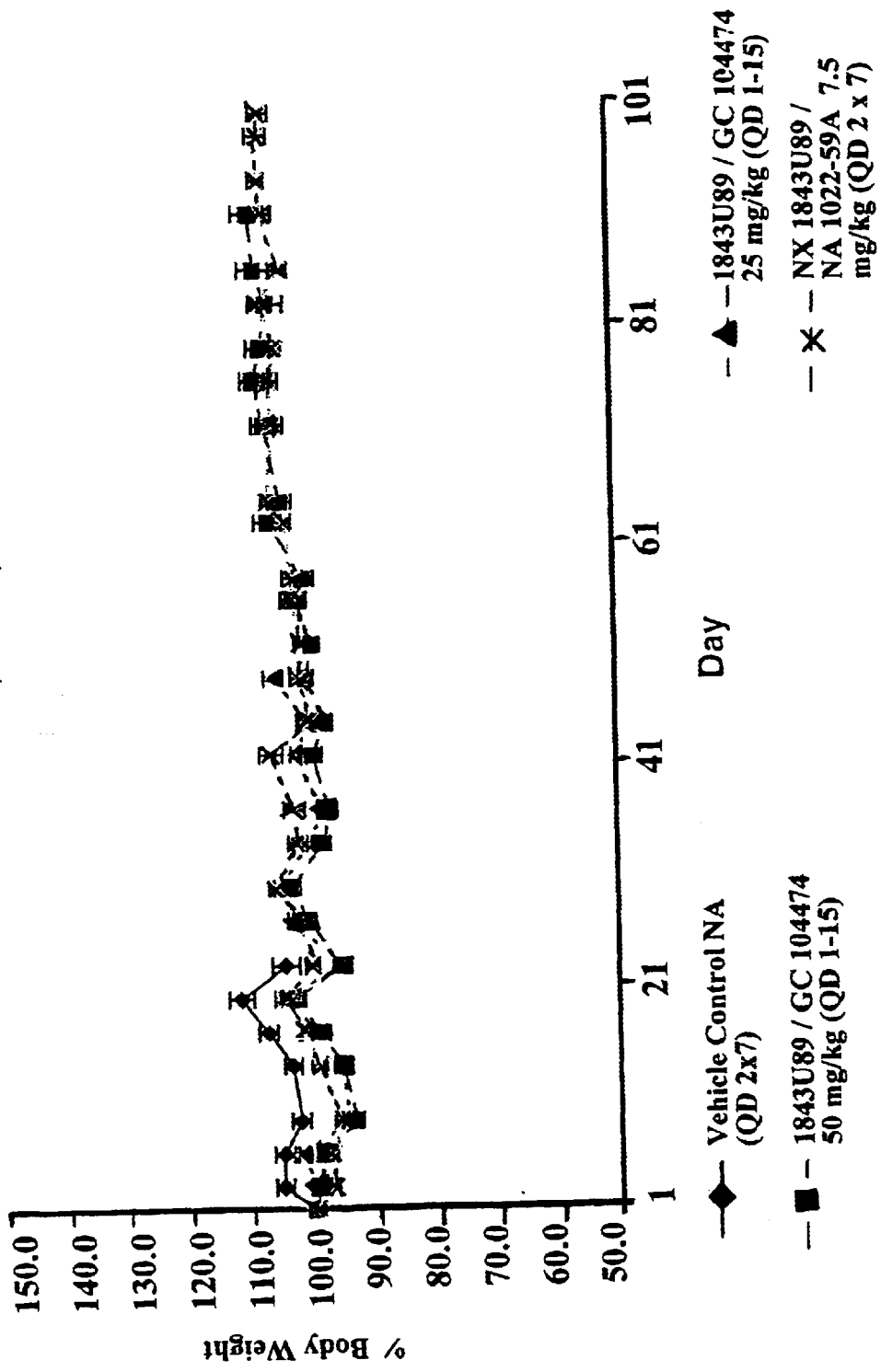
FIG. 3 depicts the effects of NX1843 and GW1843 on body weight of nude mice.

The second xenograft study compared the anti-tumor efficacy of liposomal formulated GW1843U89 (Table 1A; NA-1022-59A) dosed at 7.5 mg/kg every-other day, to free drug dosed every day at 25 and 50 mg/kg. The amount of liposomal drug allowed only 14 days of dosing (7 doses). The total amounts of free drug given were 350 mg/kg and 700 mg/kg while in the NX1843 group total drug given was 52.5 mg/kg. Table 26 summarizes the results which clearly demonstrate that the liposomal drug was more efficacious than the free drug, requiring less total drug administered on a less frequent schedule. The effects of the liposomal drug demonstrate superior efficacy to free drug, with 83% regression and log cell kill of 4.6, compared to the 25 and 50 mg/kg free drug groups, where no tumor regression occurred, and these were log cell kill values of 1.5 and 3.5, respectively. FIG. 2 shows the tumor growth curves, and demonstrates a dose response effect with free drug groups, and a more delayed tumor outgrowth with the NX 1843 group. The relative effect of the drugs on body weight is shown in FIG. 3. The body weight loss in all the drug groups was transient and reversible, never exceeding 10%.

A dose schedule study was performed with NX1843 (Table 1A; SMC-991-96), where HCT-8 tumor-bearing nude mice were dosed iv with NX1843 at the following dose and schedule: 25 mg/kg; quantity delivered 1,8; 15 mg/kg; QD(1,3,5)×2; 7.5 mg/kg; QD(1–5)×2. In addition to these dose groups the free drug was dosed at 100 mg/kg on days 1–5, and repeated for a second week. Also included in this experiment were the following: 5-fluorourcil (SFU) dosed at 100 mg/kg on days 1 and 8; a liposomal formulation of a camptothecin analog (NX211) at 6 mg/kg days 1 and 8; NX211+5FU dosed on days 1 and 8 at 6 mg/kg and 100 mg/kg, respectively; NX211 at 6 mg/kg days 1,8+free GW1843 at 100 mg/kg days 1–5×2; and NX211+NX1843 at 6 mg/kg and 25 mg/kg days 1,8. The Results are shown in Table 27. All three of the NX1843 dose groups demonstrated equivalent efficacy with log cell kill (LCK) values ranging between 3.9–4.2, with ⅛ durable cures in each group. When NX 211 was combined with either NX 1843 or GW 1843, the overall tumor effects were similar, with LCK values of 3.4. There were, however, ⅖ durable cures generated with the NX 211+NX 1843 combination. The dose groups of 5-FU alone, NX 211 alone, and GW1843 alone all were less effective in inhibiting tumor growth, with LCK values of 1.5, 1.9, and 2.4, respectively. The least effective dose groups were the 5-FU alone, NX 211 alone, and the 5-FU+NX 211 combination. The free GW 1843 dose group was slightly better in limiting tumor growth, but the greatest effect on tumor regression and overall inhibition of tumor growth were the NX 1843 dose groups, generating 5/32 durable cures. The body weight loss was transient and reversible, and never exceeded 20%. However, the NX 211 and 5-FU containing drug groups demonstrated the greatest amount of body weight loss.

Figure 4A:
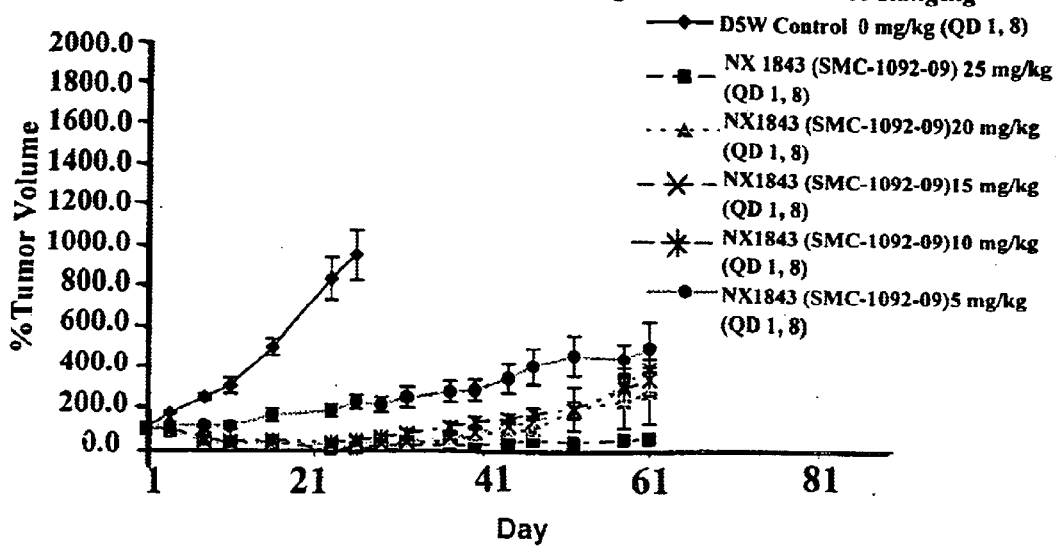
FIGS. 4A and B depicts the dose-response effects of NX1843 on tumor growth and body weight.
Figure 4B:
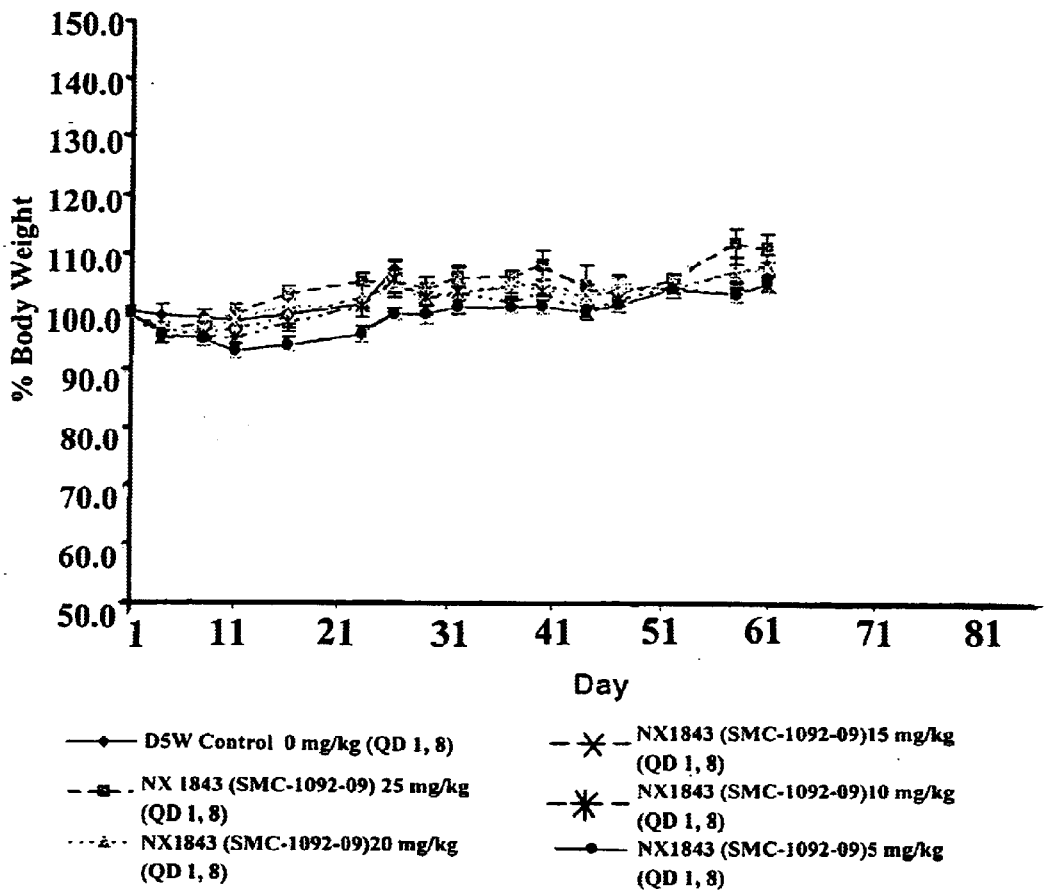

Another experiment completed with NX1843 was a dose response study where HCT-8 tumor-bearing mice were dosed iv. with NX1843 on days 1 and 8 with the following dose: 25, 20, 15, 10, 5 mg/kg. The initial tumor shrinkage was similar in all dose groups except the lowest, where tumor growth was inhibited by 80%, compared to the other 4 groups where growth was inhibited from 92–99%. There was no appreciable effect on body weight in any of the dose groups, and 7/32 cures were generated. As can be seen in FIG. 4, and Table 28, a dose dependent tumor response was evident.

Several variations in the liposomal formulation of NX 1843 have been produced and then tested in the HCT-8 xenograft model to determine if significant differences in efficacy could be determined. The variations included a range of HSPC:Cholesterol from 4:1 to 2:1, and a range in relative internal acidity from pH 5–9. The results are displayed Table 29.

This study demonstrated that no significant difference in antitumor efficacy was seen when comparing the different formulations of NX 1843 in the HCT-8 xenograft model. Pharmacokinetic differences between the different formulations tested were also minor and not significantly different.

Figure 5:
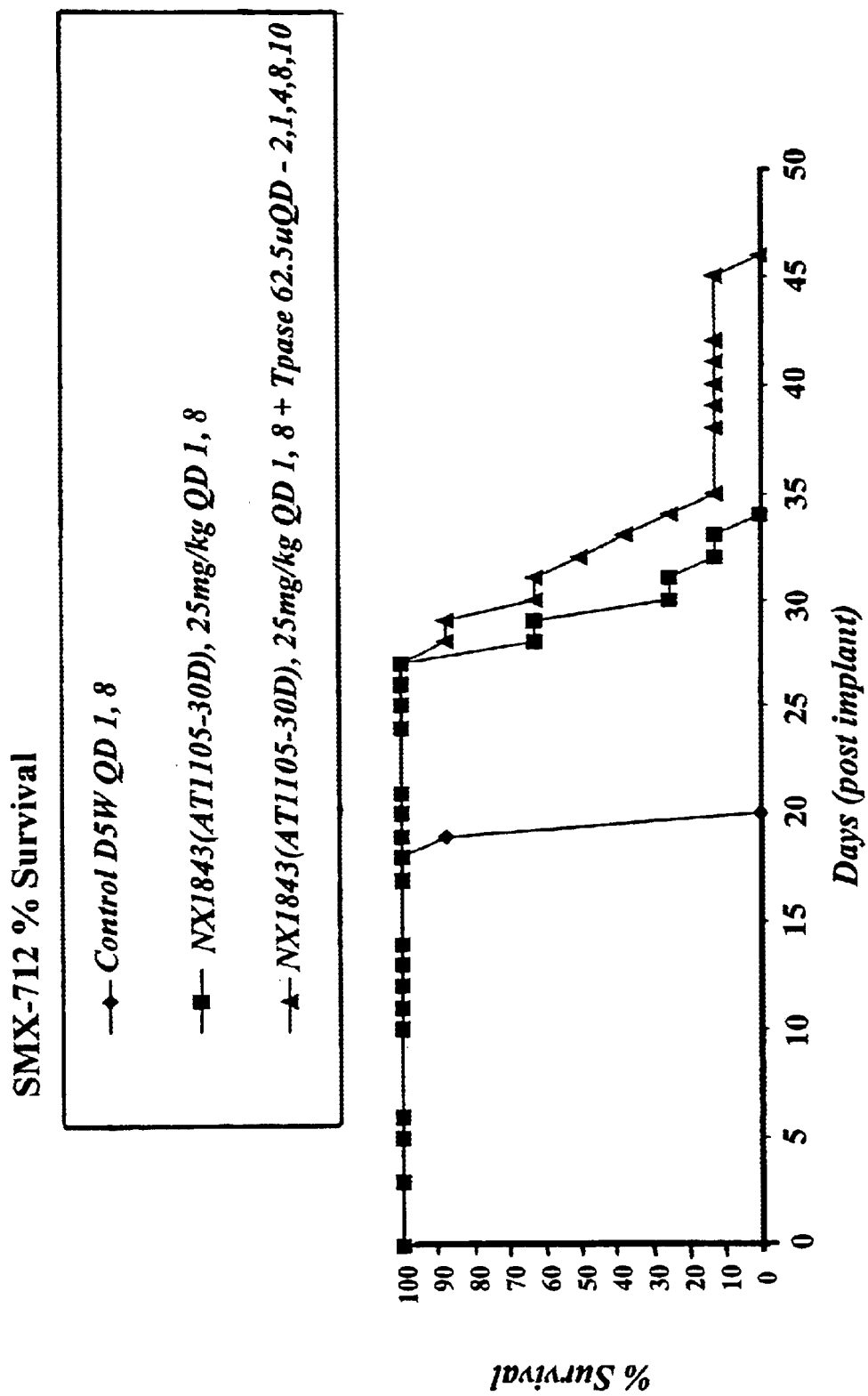
FIG. 5 depicts the efficacy of NX1843 in the molt4 leukemia model.

NX 1843 was further tested in the Molt4 leukemia model in SCID mice. In this model morbidity and mortality are the measured end points. Tumor burden is established by implanting 1×107 tumor cells iv., waiting 4 days, and then initiating treatment. The treatment groups consisted of NX 1843 at 25 mg/kg+/–thymidine phosphorylase (Tpase). The Tpase treatment lowers mouse circulating thymidine levels to that of humans (50–100 nM). The control group received D5W only. The results are shown in FIG. 5, and demonstrate that NX 1843 increases survival irrespective of Tpase treatment.

The invention claimed herein has been described with respect to particular exemplified embodiments. However, the foregoing description is not intended to limit the invention to the exemplified embodiments, and the skilled artisan should recognize that variations can be made within the scope and spirit of the invention as described in the foregoing specification. The invention includes the alternatives, modifications, and equivalents that may be included within the true spirit and scope of the invention as defined by the appended claims.

TABLE 1A

Liposomal formulations of GW1843 prepared at different HSPC:Chol molar ratios, and different pH and concentration of drug solution at hydration.

| Preparation I.D. # | HSPC:Chol Molar ratio | pH of Drug solution at hydration | Concentration of drug at hydration mg/ml | Total lipid concentration in final product mg/ml | GW1843 concentration in final product mg/ml | HSPC/Drug Mole ratio in final product | Total lipid/drug molar ratio in final product | Median Diameter nm | pH of final product |
|---|---|---|---|---|---|---|---|---|---|
| AT-1084-88B | 2:1 | 7 | 20 | 41 | 0.33 | 63 | 92 | 44 | 7.1 |
| AT-1084-86B | 4:1 | 7 | 100 | 15 | 0.51 | 17 | 21 | 57 | 5.5 |
| AT-1084-91B | 2:1 | 7 | 100 | 50 | 2.4 | 11 | 16 | 55 | 6.2 |
| AT-1084-95B | 2:1 | 7 | 100 | 44 | 1.7 | 14 | 20 | 54 | 3.2 |
| AT-1084-97B | 2:1 | 9 | 100 | 36 | 1.7 | 11 | 16 | 78 | 6.1 |
| AT-1105-32 | 4:1 | 7 | 100 | 23 | 0.74 | 13 | 17 | 54 | 6.5 |
| SMC-1092-09 | 2:1 | 7 | 100 | 59 | 3.5 | 8.9 | 13 | 43 | 7.0 |

TABLE 1A-continued

Liposomal formulations of GW1843 prepared at different HSPC:Chol molar ratios, and different pH and concentration of drug solution at hydration.

| Preparation I.D. # | HSPC:Chol Molar ratio | pH of Drug solution at hydration | Concentration of drug at hydration mg/ml | Total lipid concentration in final product mg/ml | GW1843 concentration in final product mg/ml | HSPC/Drug Mole ratio in final product | Total lipid/drug molar ratio in final product | Median Diameter nm | pH of final product |
|---|---|---|---|---|---|---|---|---|---|
| SMC-991-96 | 2:1 | 7 | 100 | 67 | 3.2 | 11 | 16 | 42 | 6.9 |
| NA-1022-63A | 2:1 | 8 | 225 | 34 | 2.0 | 8.7 | 13 | 42 | 6.1 |
| NA-1022-59A | 2:1 | 8 | 200 | 32 | 1.3 | 13 | 19 | 60 | 5.9 |
| GC-1020-36 | 2:1 | 7 | 116 | 34 | 2.2 | 8.0 | 12 | 39 | 6.0 |
| GC-1007-27 | 2:1 | 7 | 100 | 35 | 2.5 | 7.2 | 11 | 31 | 7.0 |

TABLE 1B

Additional GW1843 Liposomal Formulations

| Preparation I.D. | Lipids | Molar Ratio of lipids | GW1843 concentration mg/ml in final product | Median Diameter nm | pH |
|---|---|---|---|---|---|
| AL1230-058 | HSPC: Cholesterol | 4:1 | 2.7 | 29 | 6.5 |
| AL1230-052 | DOPC: Cholesterol | 2:1 | 1.4 | 30 | 6.3 |
| AL1230-048 | DEPC: Cholesterol | 2:1 | 1.9 | 26 | 6.9 |
| AL1230-055 | Soy-PC: Cholesterol | 2:1 | 1.5 | 43 | 6.6 |
| AL1230-041 | HSPC: Cholesterol: DSPG | 2:1:0.1 | 3.6 | 43 | 6.3 |

TABLE 1C

Liposome Formulations Containing Different Excipients

| Preparation I.D. | Excipient and concentration | pH of final final product |
|---|---|---|
| NHC1202-027-4 | 9% Sucrose | 6.5 |
| NHC1202-027-1 | 1 mM Phosphate and 9% Sucrose | 7.5 |
| NHC1202-027-2 | 5 mM Phosphate and 9% Sucrose | 7.7 |
| NHC1202-027-3 | 1 mM Citrate and 9% sucrose | 7.1 |
| NHC1202-089-2 | 1 mM Succinate and 9% sucrose | 6.6 |

TABLE 1D

Median Diameter Stability (2–8° C.) of Liposome Formulations Containing Different Excipients

| Preparation I.D. | T = 0 | T = 3 Months |
|---|---|---|
| NHC1202-027-4 | 35 | 36 |
| NHC1202-027-1 | 37 | 40 |
| NHC1202-027-2 | 37 | 41 |
| NHC1202-027-3 | 38 | 39 |
| NHC1202-089-2 | 37 | 46 (1 month) |

TABLE 2

GW1843 Plasma Concentrations in Rats Following a Single 1 mg/kg Intravenous Bolus Dose in Rats.

| Group | Free GW1843 | | | Liposome pH 7.0 | | | Liposome pH 7.3 | | | Liposome pH 7.4 | | | Liposome pH 7.5 | | |
|---|---|---|---|---|---|---|---|---|---|---|---|---|---|---|---|
| Animal # | 1 | 2 | 3 | 4 | 5 | 6 | 7 | 8 | 9 | 10 | 11 | 12 | 13 | 14 | 15 |
| Time (h) | | | | | | GW1843 Plasma Concentration (µg/mL) | | | | | | | | | |
| 0.083 | 0.52 | 0.76 | 0.76 | | | | | | | | | | | | |
| 0.250 | 0.18 | 0.20 | 0.19 | | | | | | | | | | | | |
| 0.500 | 0.10 | 0.11 | 0.10 | | | | | | | | | | | | |
| 1.000 | BLQ | 0.06 | 0.06 | | | | | | | | | | | | |
| 0.166 | | | | 13.2 | 14.0 | 16.1 | 22.2 | 22.2 | 21.8 | 18.3 | 17.2 | 19.9 | 24.1 | 22.2 | 22.3 |
| 0.750 | | | | 10.7 | 10.8 | 11.7 | 16.0 | 16.1 | 16.2 | 18.6 | 17.1 | 18.8 | 15.5 | 17.0 | 19.1 |
| 2.000 | | | | 7.98 | 8.22 | 9.14 | 14.7 | 12.5 | 12.1 | 15.3 | 12.5 | 14.5 | 14.7 | 16.9 | 17.8 |
| 4.000 | | | | 7.38 | 8.15 | 9.07 | 11.9 | 12.9 | 11.3 | 12.1 | 10.8 | 13.7 | 13.6 | 15.2 | 14.8 |
| 8.000 | | | | 6.35 | 7.49 | 7.53 | 11.1 | 12.6 | 11.3 | 12.2 | 10.6 | 12.1 | 14.0 | 13.4 | 13.5 |
| 24.00 | | | | 3.75 | 3.74 | 4.27 | 6.10 | 6.52 | 5.96 | 6.87 | 5.13 | 6.74 | 6.75 | 7.06 | 6.84 |
| 32.00 | | | | 3.23 | 3.02 | 3.25 | 4.07 | 4.32 | 4.27 | 4.36 | 4.19 | 4.96 | 4.69 | 4.86 | 4.37 |
| 48.00 | | | | 1.61 | 1.54 | 1.84 | 2.71 | 2.77 | 2.63 | 2.27 | 2.44 | 3.02 | 3.14 | 3.00 | 2.69 |

TABLE 3

Pharmacokinetic Parameters by Noncompartmental Analysis for GW1843 Following a Single 1 mg/kg Intravenous Bolus Dose in Rats.

| | AUCinf (h × ng/mL) | AUClast (h × ng/mL) | Cl (mL/h × kg) | Cmax (ng/mL) | MRTinf (h) | t½ (h) | Vss (mL/kg) |
|---|---|---|---|---|---|---|---|
| Free Drug | 263 | 219 | 3805 | 1281 | 0.5 | 0.5 | 1886.8 |
| lipo pH 7.0 | 266740 | 220640 | 3.75 | 15548 | 27.4 | 19.2 | 102.6 |
| lipo pH 7.3 | 412307 | 339339 | 2.43 | 24124 | 27.3 | 18.7 | 66.2 |
| lipo pH 7.4 | 412188 | 344089 | 2.43 | 18541 | 26.5 | 18.3 | 64.3 |
| lipo pH 7.5 | 462920 | 387013 | 2.16 | 24790 | 26.1 | 17.9 | 56.3 |

TABLE 4

GW1843 Plasma Concentrations following a Single 1 mg/kg Intravenous Bolus Dose of Free GW1843 in Male Sprague-Dawley Rats.

Concentration of GW1843 in Plasma (µg/mL)

| Time (hr) | Rat 1 | Rat 2 | Rat 3 | Rat 4 | MEAN | SD |
|---|---|---|---|---|---|---|
| 0.083 | 0.991 | 0.823 | 1.02 | 0.974 | 0.952 | 0.088 |
| 0.250 | 0.214* | 0.212 | 0.270 | 0.325 | 0.255 | 0.054 |
| 0.500 | 0.117 | 0.091** | 0.127 | 0.138 | 0.118 | 0.020 |

*Sample actually taken at 0.267 hr.
**Data below established LLQ (0.1 µg/mL). Value obtained by extrapolation.

TABLE 5

Total GW1843 Plasma Concentrations following a Single 1 mg/kg Intravenous Bolus Dose of Liposome Encapsulate GW1843 (NX1843; SMC-991–96) in Male Sprague-Dawley Rats.

Concentration of GW1843 in Plasma (µg/mL)

| Time (hr) | Rat 5 | Rat 6 | Rat 7 | Rat 8 | MEAN | SD |
|---|---|---|---|---|---|---|
| 0.167 | 21.0 | 23.9 | 26.6 | 23.7 | 23.8 | 2.29 |
| 0.500 | 22.1 | 23.3 | 22.9 | 20.8 | 22.3 | 1.10 |
| 1.500 | 15.7 | 21.1 | 21.6 | 18.0 | 19.1 | 2.77 |
| 4.000 | 17.9 | 17.8 | 17.9 | 16.3 | 17.5 | 0.78 |
| 7.966 | 14.0 | 15.6 | 17.2 | 13.9 | 15.2 | 1.56 |
| 24.18 | 7.22 | 8.17 | 8.64 | 7.09 | 7.78 | 0.75 |
| 31.98 | 5.21 | 7.64 | 6.71 | 5.96 | 6.38 | 1.04 |
| 48.50 | 2.36 | 3.25 | 3.19 | 2.77 | 2.89 | 0.41 |
| 72.55 | 1.01 | 1.40 | 1.42 | 1.13 | 1.24 | 0.20 |
| 96.33 | 0.329 | 0.460 | 0.487 | 0.277 | 0.388 | 0.101 |

TABLE 6

Plasma Pharmacokinetic Parameters for GW1843 Following a Single 1 mg/kg Intravenous Bolus Dose of Free GW1843 in Male Sprague-Dawley Rats (Non-compartmental Analysis).

| Animal Number Parameter | Rat 1 | Rat 2 | Rat 3 | Rat 4 | Mean | SD |
|---|---|---|---|---|---|---|
| Weight (kg) | 0.38112 | 0.39144 | 0.38346 | 0.34391 | 0.37498 | 0.021 |
| AUC(0-inf) (µg.hr/mL) | 0.27 | 0.23 | 0.29 | 0.29 | 0.27 | 0.028 |
| AUC(0-last) (µg.hr/mL) | 0.25 | 0.21 | 0.26 | 0.26 | 0.25 | 0.024 |
| CL (mL/hr.kg) | 3,660 | 4,410 | 3,470 | 3,430 | 3,740 | 456 |
| Cmax (µg/mL) | 1.99 | 1.62 | 1.98 | 1.69 | 1.82 | 0.193 |
| MRT(0-inf) (hr) | 0.18 | 0.17 | 0.19 | 0.21 | 0.19 | 0.017 |
| T½ (hr) | 0.14 | 0.14 | 0.14 | 0.15 | 0.14 | 0.005 |
| Vss (mL/kg) | 654 | 762 | 650 | 709 | 694 | 52.9 |

TABLE 7

Plasma Pharmacokinetic Parameters for GW1843 Following a Single 1 mg/kg Intravenous Bolus Dose of Liposome Encapsulated GW1843 (NX1843; SMC-991-96) in Male Sprague-Dawley Rats (Non-compartmental Analysis).

| Animal Number Parameter | Rat 5 | Rat 6 | Rat 7 | Rat 8 | Mean | SD |
|---|---|---|---|---|---|---|
| Weight (kg) | 0.39031 | 0.38086 | 0.37256 | 0.42019 | 0.39098 | 0.021 |
| AUC(0-inf) (µg.hr/mL) | 469 | 565 | 578 | 482 | 524 | 55.9 |
| AUC(0-last) (µg.hr/mL) | 461 | 554 | 566 | 478 | 515 | 52.9 |
| CL (mL/hr.kg) | 2.13 | 1.77 | 1.73 | 2.08 | 1.93 | 0.21 |
| Cmax (µg/mL) | 22.1 | 24.3 | 28.7 | 25.3 | 25.1 | 2.75 |
| MRT(0-inf) (hr) | 23.6 | 25.7 | 25.3 | 24.1 | 24.7 | 0.99 |
| T½ (hr) | 16.4 | 17.0 | 17.5 | 15.5 | 16.6 | 0.86 |
| Vss (mL/kg) | 50.4 | 45.5 | 43.8 | 50.0 | 47.4 | 3.28 |

TABLE 8

Total GW1843 Plasma Concentrations in Male Sprague-Dawley Rats Following a 1 mg/kg I.V. Bolus Administration of Liposome Encapsulated GW1843 (NX1843) Lot SMC-1092-09.

Concentration of NX1843 in Plasma (µg/mL)

| Time (hr) | Rat 5 | Rat 6 | Rat 7 | Rat 8 | MEAN | SD |
|---|---|---|---|---|---|---|
| 0.183 | 16.9 | 15.8 | 15.5 | 20.3 | 17.1 | 2.20 |
| 0.517 | 13.2 | 13.5 | 13.2 | 16.0 | 14.0 | 1.36 |
| 1.650 | 11.7 | 12.1 | 11.6 | 11.5 | 11.7 | 0.263 |
| 4.100 | 10.3 | 9.7 | 10.3 | 11.0 | 10.3 | 0.532 |
| 8.000 | 8.51 | 8.34 | 8.72 | 9.96 | 8.88 | 0.735 |
| 24.000 | 4.79 | 4.27 | 4.32 | 5.71 | 4.77 | 0.667 |
| 32.000 | 3.32 | 2.86 | 2.57 | 2.72 | 2.87 | 0.324 |
| 48.167 | 1.48 | 1.08 | 1.06 | 1.32 | 1.24 | 0.202 |
| 72.200 | 0.379 | 0.250 | BLOQ | BLOQ | — | — |
| 96.000 | BLOQ | BLOQ | BLOQ | BLOQ | — | — |

BLOQ-Below limit of quantification

TABLE 9

Total GW1843 Plasma Concentrations in Male Sprague-Dawley Rats Following a 1 mg/kg I.V. Bolus Administration of Liposome Encapsulated GW1843 (NX1843) Lot SMC-991-96.

| Time (hr) | Concentration of NX1843 in Plasma ($\mu$g/mL) | | | | | |
|---|---|---|---|---|---|---|
| | Rat 5 | Rat 6 | Rat 7 | Rat 8 | MEAN | SD |
| 0.183 | 18.0 | 15.9 | 15.1 | 14.6 | 15.9 | 1.50 |
| 0.500 | 17.0* | 13.0 | 14.2 | 13.8 | 14.5 | 1.74 |
| 1.650 | 15.5 | 13.3 | 10.6 | 12.2 | 12.9 | 2.06 |
| 4.100 | 13.2 | 10.5 | 10.2 | 10.7 | 11.2 | 1.38 |
| 8.000 | 11.8 | 7.8 | 9.5 | 9.5 | 9.7 | 1.64 |
| 24.000 | 6.00 | 4.20 | 5.17 | 4.45 | 4.96 | 0.809 |
| 32.000 | 4.31 | 2.21 | 2.97 | 3.24 | 3.18 | 0.869 |
| 48.167 | 1.80 | 0.864 | 1.32 | 1.11 | 1.27 | 0.397 |
| 72.200 | 0.470 | BLOQ | 0.247 | BLOQ | — | — |
| 96.000 | BLOQ | BLOQ | BLOQ | BLOQ | — | — |

*Sample taken at 0.517 minutes
BLOQ-Below limit of quantification.

TABLE 12

Total GW1843 Plasma Concentrations in Male Sprague-Dawley Rats (Group A) Following a Single 1 mg/kg I.V. Bolus Administration of a Liposome Encapsulated GW1843 (NX1843) Formulation with a High Internal pH (Lot AT-1084-97B).

| Time (hr) | Concentration of GW1843 in Plasma ($\mu$g/mL) | | | | | |
|---|---|---|---|---|---|---|
| | Rat 1 | Rat 2 | Rat 3 | Rat 4 | MEAN | SD |
| 0.167 | 16.6 | 18.5 | 19.4 | 15.1 | 17.4 | 1.93 |
| 0.500 | 15.6 | 14.9 | 15.5 | 14.2 | 15.1 | 0.645 |
| 1.567 | 12.6* | 13.7 | 15.3 | 12.0** | 13.4 | 1.45 |
| 4.000 | 11.9 | 10.5 | 12.9 | 11.1 | 11.6 | 1.04 |
| 7.550 | 10.5 | 10.7 | 10.8 | 9.06 | 10.3 | 0.813 |
| 24.067 | 4.78 | 5.07 | 5.31 | 4.41 | 4.89 | 0.388 |
| 31.917 | 2.03 | 2.81 | 3.38 | 2.94 | 2.79 | 0.562 |
| 48.283 | 0.764 | 1.10 | 1.14 | 0.799 | 0.951 | 0.197 |
| 72.250 | 0.135 | 0.180 | 0.185 | BLOQ | 0.167+ | 0.028+ |
| 96.000 | NS | NS | NS | NS | — | — |

BLOQ-Below limit of quantification
NS-No sample
*Sample taken at 1.583 hr.

TABLE 10

Plasma Pharmacokinetic Parameters for GW1843 Following a Single 1 mg/kg Intravenous Bolus Dose of Liposome Encapsulated GW1843 (NX1843), Lot SMC-1092-09, in Male Sprague-Dawley Rats (Non-compartmental Analysis).

| Parameter | Animal Number | | | | | |
|---|---|---|---|---|---|---|
| | Rat 1 | Rat 2 | Rat 3 | Rat 4 | Mean | SD |
| Weight (kg) | 0.22475 | 0.20796 | 0.21927 | 0.20716 | 0.21479 | 0.00864 |
| AUC(0-inf) ($\mu$g.hr/mL) | 285 | 257 | 259 | 302 | 276 | 21.7 |
| AUC(0-last) ($\mu$g.hr/mL) | 278 | 253 | 240 | 280 | 263 | 19.5 |
| CL (mL/hr.kg) | 3.51 | 3.89 | 3.87 | 3.31 | 3.65 | 0.283 |
| Cmax ($\mu$g/mL) | 19.4 | 17.2 | 16.9 | 23.1 | 19.2 | 2.86 |
| MRT(0-inf) (hr) | 21.0 | 18.9 | 18.7 | 19.2 | 19.5 | 1.05 |
| T½ (hr) | 13.1 | 11.7 | 12.0 | 11.9 | 12.2 | 0.63 |
| Vss (mL/kg) | 73.8 | 73.5 | 72.5 | 63.4 | 70.8 | 4.96 |

TABLE 11

Plasma Pharmacokinetic Parameters for GW1843 Following a Single 1 mg/kg Intravenous Bolus Dose of Liposome Encapsulated GW1843 (NX1843), Lot SMC-991-96, in Male Sprague-Dawley Rats (Non-compartmental Analysis).

| Parameter | Animal Number | | | | | |
|---|---|---|---|---|---|---|
| | Rat 5 | Rat 6 | Rat 7 | Rat 8 | Mean | SD |
| Weight (kg) | 0.21681 | 0.21542 | 0.21783 | 0.21085 | 0.21523 | 0.00308 |
| AUC(0-inf) ($\mu$g.hr/mL) | 368 | 241 | 284 | 278 | 293 | 53.6 |
| AUC(0-last) ($\mu$g.hr/mL) | 360 | 228 | 280 | 259 | 282 | 56.4 |
| CL (mL/hr.kg) | 2.72 | 4.15 | 3.53 | 3.60 | 3.50 | 0.589 |
| Cmax ($\mu$g/mL) | 18.4 | 17.9 | 15.6 | 15.0 | 16.7 | 1.68 |
| MRT(0-inf) (hr) | 20.6 | 17.2 | 19.2 | 18.9 | 19.0 | 1.40 |
| T½ (hr) | 13.0 | 10.8 | 11.2 | 11.8 | 11.7 | 0.96 |
| Vss (mL/kg) | 56.0 | 71.4 | 67.7 | 68.1 | 65.8 | 6.74 |

TABLE 12-continued

Total GW1843 Plasma Concentrations in Male Sprague-Dawley Rats (Group A) Following a Single 1 mg/kg I.V. Bolus Administration of a Liposome Encapsulated GW1843 (NX1843) Formulation with a High Internal pH (Lot AT-1084-97B).

Concentration of GW1843 in Plasma (μg/mL)

| Time (hr) | Rat 1 | Rat 2 | Rat 3 | Rat 4 | MEAN | SD |
|---|---|---|---|---|---|---|

**Sample taken at 1.550 hr.
+Mean and SD of three determined values.

TABLE 13

Total GW1843 Plasma Concentrations in Male Sprague-Dawley Rats (Group B) Following a Single 1 mg/kg I.V. Bolus Administration of the Standard Formulation of Liposome Encapsulated GW1843 (NX1843) (Lot SMC-1092-09).

Concentration of GW1843 in Plasma (μg/mL)

| Time (hr) | Rat 5 | Rat 6 | Rat 7 | Rat 8 | MEAN | SD |
|---|---|---|---|---|---|---|
| 0.167 | 16.9 | 12.1 | 14.1 | 18.5 | 15.4 | 2.85 |
| 0.500 | 15.1 | 11.9 | 12.3 | 16.7 | 14.0 | 2.29 |
| 1.500 | 13.8 | 10.4 | 10.6 | 14.5 | 12.3 | 2.13 |
| 3.967 | 12.3 | 10.3 | 11.1 | 11.3 | 11.3 | 0.823 |
| 8.000 | 8.07 | 7.79 | 9.08 | 11.0 | 8.99 | 1.45 |
| 24.067 | 3.77 | 3.61 | 4.17 | 3.85 | 3.85 | 0.236 |
| 32.067 | 2.49 | 2.36 | 2.25 | 3.40 | 2.63 | 0.526 |
| 48.167 | 0.766 | 0.922 | 0.932 | 1.17 | 0.948 | 0.973 |
| 72.917 | 0.109 | 0.133 | 0.177 | 0.259 | 0.170 | 0.066 |
| 96.250 | BLOQ | BLOQ | BLOQ | BLOQ | — | — |

BLOQ-Below limit of quantification.

TABLE 14

Total GW1843 Plasma Concentrations in Male Sprague-Dawley Rats (Group C) Following a Single 1 mg/kg I.V. Bolus Administration of the Standard Formulation of Liposome Encapsulated GW1843 (NX1843) (Lot AT-1084-91B).

Concentration of GW1843 in Plasma (μg/mL)

| Time (hr) | Rat 9 | Rat 10 | Rat 11 | Rat 12 | MEAN | SD |
|---|---|---|---|---|---|---|
| 0.167 | 20.5 | 17.6 | 18.4 | 21.3 | 19.5 | 1.74 |
| 0.517 | 19.4* | 13.1** | 17.4 | 20.8 | 17.7 | 3.35 |
| 1.500 | 15.7 | 12.4 | 14.7 | 14.9 | 14.4 | 1.42 |
| 3.967 | 16.2 | 11.5 | 13.4 | 15.7 | 14.2 | 2.17 |
| 8.000 | 11.9 | 9.51 | 11.5 | 13.7 | 11.7 | 1.72 |
| 24.017 | 6.33 | 4.59 | 5.68 | 6.45 | 5.76 | 0.852 |
| 32.067 | 3.92 | 2.70 | 3.85 | 4.06 | 3.63 | 0.628 |
| 48.167 | 1.83 | 0.974 | 1.53 | 1.73 | 1.52 | 0.382 |
| 72.917 | 0.299 | 0.273 | 0.291 | 0.403 | 0.317 | 0.059 |
| 96.250 | BLOQ | BLOQ | BLOQ | BLOQ | — | — |

BLOQ-Below limit of quantification
*Sample taken at 0.500 hr.
**Sample taken at 0.583 hr.

TABLE 15

Total GW1843 Plasma Concentrations in Male Sprague-Dawley Rats (Group D) Following a Single 1 mg/kg I.V. Bolus Administration of a Liposome Encapsulated GW1843 (NX1843) Formulation with a High Lipid:Drug Ratio (Lot AT-1084-88B).

Concentration of GW1843 in Plasma (μg/mL)

| Time (hr) | Rat 13 | Rat 14 | Rat 15 | Rat 16 | MEAN | SD |
|---|---|---|---|---|---|---|
| 0.167 | 14.3 | 14.5 | 16.8 | 15.5 | 15.3 | 1.14 |
| 0.500 | 12.1 | 12.5 | 12.0 | 12.7 | 12.3 | 0.330 |
| 1.550 | 10.7 | 10.2 | 10.9 | 7.34* | 9.79 | 1.66 |
| 4.000 | 7.95 | 7.75 | 9.10 | 6.55 | 7.84 | 1.04 |
| 7.550 | 6.61 | 6.30 | 6.53 | 3.51 | 5.74 | 1.49 |
| 24.067 | 2.58 | 2.53 | 2.11 | 1.68 | 2.23 | 0.420 |
| 31.917 | 1.62 | 1.69 | 1.66 | 1.24 | 1.55 | 0.210 |
| 48.283 | 0.674 | 0.636 | 0.561 | 0.432 | 0.576 | 0.107 |
| 72.250 | 0.250 | 0.239 | 0.187 | 0.138 | 0.204 | 0.052 |
| 96.000 | NS | NS | NS | NS | — | — |

NS-No Sample
*Sample taken at 1.533 hr.

TABLE 16

Total GW1843 Plasma Concentrations in Large Male Sprague-Dawley Rats (Group E) Following a Single 1 mg/kg I.V. Bolus Administration of the Formulation of Liposome Encapsulated GW1843 (NX1843) (Lot AT-1084-91B).

Concentration of GW1843 in Plasma (μg/mL)

| Time (hr) | Rat 17 | Rat 18 | Rat 19 | Rat 20 | MEAN | SD |
|---|---|---|---|---|---|---|
| 0.167 | 24.9 | 23.3 | 22.8 | 24.7 | 23.9 | 1.03 |
| 0.517 | 22.1 | 22.4 | 19.7 | 21.8 | 21.5 | 1.22 |
| 1.500 | 12.1 | 19.0 | 14.4* | 18.0* | 15.9 | 3.20 |
| 3.967 | 15.4 | ND | 17.5 | ND | 16.5+ | 1.48+ |
| 8.000 | 19.3 | 10.6 | 15.4 | 14.0 | 14.8 | 3.60 |
| 24.017 | 9.27 | 10.0 | 7.89 | 11.7 | 9.72 | 1.59 |
| 32.067 | 7.19 | 7.07 | 6.45 | 8.43 | 7.29 | 0.829 |
| 48.167 | 3.94 | 3.06 | 2.56 | 4.58 | 3.54 | 0.900 |
| 72.917 | 1.30 | 1.11 | 0.660 | 1.73 | 1.20 | 0.444 |
| 96.250 | 0.317 | 0.347 | 0.390 | 0.127 | 0.295 | 0.116 |

ND-No Data
*Sample taken at 1.533 hr.
+Mean and SD of the two data points determined.

TABLE 17

Plasma Pharmacokinetic Parameters (Non-compartmental Analysis) for Total GW1843 Following a Single 1 mg/kg I.V. Bolus Dose of a Liposome Encapsulated GW1843 (NX1843) Formulation with a High Internal pH (Lot AT-1084-97B) in Male Sprague-Dawley Rats (Group A).

| Parameter | Rat 1 | Rat 2 | Rat 3 | Rat 4 | Mean | SD |
|---|---|---|---|---|---|---|
| Weight (kg) | 0.22201 | 0.20778 | 0.22268 | 0.22589 | 0.21959 | 0.00805 |
| AUC(0-int) ($\mu$g.hr/mL) | 270 | 290 | 312 | 258 | 283 | 23.7 |
| AUC(0-last) ($\mu$g.hr/mL) | 268 | 288 | 309 | 247 | 278 | 26.6 |
| CL (mL/hr.kg) | 3.71 | 3.45 | 3.20 | 3.87 | 3.56 | 0.295 |
| Cmax ($\mu$g/mL) | 17.1 | 20.6 | 21.7 | 15.6 | 18.8 | 2.87 |
| MRT(0-inf) (hr) | 15.8 | 17.5 | 17.4 | 17.0 | 16.9 | 0.780 |
| T½ (hr) | 9.67 | 10.1 | 9.89 | 9.64 | 9.83 | 0.215 |
| Vss (mL/kg) | 58.7 | 60.2 | 55.7 | 65.8 | 60.1 | 4.24 |

TABLE 18

Plasma Pharmacokinetic Parameters (Non-compartmental Analysis) for Total GW1843 Following a Single 1 mg/kg I.V. Bolus Dose of the Standard Liposome Encapsulated GW1843 (NX1843), Formulation (Lot SMC-1092-09) in Male Sprague-Dawley Rats (Group B).

| Parameter | Rat 5 | Rat 6 | Rat 7 | Rat 8 | Mean | SD |
|---|---|---|---|---|---|---|
| Weight (kg) | 0.23104 | 0.22129 | 0.22358 | 0.22141 | 0.22433 | 0.00460 |
| AUC(0-inf) ($\mu$g.hr/mL) | 244 | 226 | 250 | 293 | 253 | 28.4 |
| AUC(0-last) ($\mu$g.hr/mL) | 243 | 224 | 247 | 288 | 251 | 26.9 |
| CL (mL/hr.kg) | 4.10 | 4.42 | 4.00 | 3.42 | 3.99 | 0.417 |
| Cmax ($\mu$g/mL) | 17.9 | 12.2 | 15.1 | 19.5 | 16.2 | 3.21 |
| MRT(0-inf) (hr) | 16.0 | 17.5 | 17.5 | 18.3 | 17.3 | 0.960 |
| T½ (hr) | 9.42 | 10.2 | 10.9 | 12.0 | 10.6 | 1.10 |
| Vss (mL/kg) | 65.4 | 77.3 | 69.9 | 62.5 | 68.8 | 6.45 |

TABLE 19

Plasma Pharmacokinetic Parameters (Non-compartmental Analysis) for Total GW1843 Following a Single 1 mg/kg I.V. Bolus Dose of the Standard Liposome Encapsulated GW1843 (NX1843) Formulation (Lot AT-1084-91B) in Male Sprague-Dawley Rats (Group C).

| Animal Number Parameter | Rat 9 | Rat 10 | Rat 11 | Rat 12 | Mean | SD |
|---|---|---|---|---|---|---|
| Weight (kg) | 0.22583 | 0.22876 | 0.22839 | 0.22250 | 0.22637 | 0.00289 |
| AUC(0-inf) ($\mu$g.hr/mL) | 375 | 275 | 344 | 395 | 347 | 52.5 |
| AUC(0-last) ($\mu$g.hr/mL) | 370 | 271 | 339 | 387 | 342 | 51.2 |
| CL (mL/hr.kg) | 2.67 | 3.63 | 2.91 | 2.53 | 2.94 | 0.489 |
| Cmax ($\mu$g/mL) | 21.1 | 19.8 | 18.9 | 21.6 | 20.4 | 1.23 |
| MRT (0-inf) (hr) | 18.9 | 18.3 | 18.9 | 19.3 | 18.9 | 0.412 |
| T½ (hr) | 11.2 | 12.0 | 11.3 | 12.3 | 11.7 | 0.535 |
| Vss (mL/kg) | 50.3 | 66.5 | 55.1 | 48.8 | 55.2 | 8.01 |

TABLE 20

Plasma Pharmacokinetic Parameters (Non-compartmental Analysis) for Total GW1843 Following a Single 1 mg/kg I.V. Bolus Dose of a Liposome Encapsulated GW1843 (NX1843) Formulation with a High Lipid:Drug Ratio (Lot AT-1084-88B) in Male Sprague-Dawley Rats (Group D).

| Animal Number Parameter | Rat 13 | Rat 14 | Rat 15 | Rat 16 | Mean | SD |
|---|---|---|---|---|---|---|
| Weight (kg) | 0.22711 | 0.22021 | 0.21770 | 0.21706 | 0.22052 | 0.00460 |
| AUC(0-inf) ($\mu$g.hr/mL) | 187 | 183 | 180 | 126 | 169 | 28.8 |
| AUC(0-last) ($\mu$g.hr/mL) | 182 | 179 | 178 | 124 | 166 | 27.9 |
| CL (mL/hr.kg) | 5.34 | 5.47 | 5.54 | 7.92 | 6.07 | 1.24 |
| Cmax ($\mu$g/mL) | 15.5 | 15.6 | 19.9 | 17.1 | 17.0 | 2.05 |
| MRT(0-inf) (hr) | 18.5 | 18.0 | 16.4 | 16.9 | 17.5 | 0.968 |
| T½ (hr) | 14.4 | 11.4 | 10.3 | 10.6 | 11.7 | 1.88 |
| Vss (mL/kg) | 98.8 | 98.5 | 90.9 | 133 | 105 | 18.8 |

TABLE 21

Plasma Pharmacokinetic Parameters (Non-compartmental Analysis) for Total GW1843 Following a Single 1 mg/kg I.V. Bolus Dose of the Standard Liposome Encapsulated GW1843 (NX1843) Formulation (Lot AT-1084-91B) in 0.4 kg Male Sprague-Dawley Rats (Group E).

| Animal Number Parameter | Rat 17 | Rat 18 | Rat 19 | Rat 20 | Mean | SD |
|---|---|---|---|---|---|---|
| Weight (kg) | 0.41828 | 0.40312 | 0.41142 | 0.40424 | 0.40927 | 0.00705 |
| AUC(0-inf) ($\mu$g.hr/mL) | 586 | 506 | 494 | 611 | 549 | 58.0 |
| AUC(0-last) ($\mu$g.hr/mL) | 579 | 499 | 485 | 609 | 543 | 60.4 |
| CL (mL/hr.kg) | 1.71 | 1.98 | 2.02 | 1.64 | 1.84 | 0.191 |
| Cmax ($\mu$g/mL) | 26.4 | 23.7 | 24.4 | 26.2 | 25.2 | 1.33 |
| MRT(0-inf) (hr) | 24.9 | 25.5 | 23.3 | 25.5 | 24.8 | 1.04 |
| T½ (hr) | 14.3 | 15.0 | 15.5 | 11.0 | 14.0 | 2.03 |
| Vss (mL/kg) | 42.6 | 50.3 | 47.2 | 41.7 | 45.5 | 4.03 |

TABLE 22

Summary Table of the Total GW1843 Plasma Pharmacokinetic Parameters Obtained Following a Single 1 mg/kg Intravenous Bolus Dose of the Standard Liposome Encapsulated GW1843 (NX1843) Formulation in 220 gram Male Sprague-Dawley Rats (Non-compartmental Analysis).

| Parameter | NX1843 Study # R990198-138E Lot: SMC-1092-09 | NX1843 Study # R990198-138E Lot: SMC-991-96 | NX1843 Study # R2000007-138E Lot: SMC-1092-09 | NX1843 Study # R2000007-138E Lot: AT-1084-91B |
|---|---|---|---|---|
| n | 4 | 4 | 4 | 4 |
| Weight (kg) | 0.215 ± 0.00864 | 0.215 ± 0.00308 | 0.224 ± 0.0046 | 0.226 ± 0.0029 |
| Dose (mg/kg) | 1.00 | 1.00 | 1.00 | 1.00 |
| Cmax ($\mu$g/mL) | 19.1 ± 2.86 | 16.8 ± 1.70 | 16.2 ± 3.21 | 20.4 ± 1.23 |
| AUC(0-inf) ($\mu$g.hr/mL) | 276 ± 21.9 | 293 ± 53.8 | 253 ± 28.4 | 347 ± 51.2 |
| AUC(0-last) ($\mu$g.hr/mL) | 263 ± 19.3 | 281 ± 56.2 | 251 ± 26.9 | 342 ± 56.2 |
| CL (mL/hr.kg) | 3.65 ± 0.283 | 3.50 ± 0.589 | 3.99 ± 0.417 | 2.94 ± 0.489 |
| T½ (hr) | 12.2 ± 0.06 | 11.7 ± 0.96 | 10.6 ± 1.10 | 11.7 ± 0.535 |
| Vss (mL/kg) | 70.8 ± 5.00 | 65.8 ± 6.74 | 68.8 ± 6.45 | 55.2 ± 8.01 |

TABLE 23

Summary Table of the Total GW1843 Plasma Pharmacokinetic Parameters Obtained Following a Single 1 mg/kg Intravenous Bolus Dose of the Standard Liposome Encapsulated GW1843 (NX1843) Formulation in small (220 gram) versus Large (400 g) Male Sprague-Dawley Rats (Non-compartmental Analysis).

| Parameter | NX1843 Study # R990198-138E Lot: SMC-991-96 | NX1843 Study # R990164-138E Lot: SMC-991-96 | NX1843 Study # R2000007-138E Lot: AT-1084-91B | NX1843 Study # R2000007-138E Lot: AT-1084-91B |
|---|---|---|---|---|
| n | 4 | 4 | 4 | 4 |
| Weight (kg) | 0.215 ± 0.00308 | 0.391 ± 0.021 | 0.226 ± 0.0029 | 0.4093 ± 0.0071 |
| Dose (mg/kg) | 1.00 | 1.00 | 1.00 | 1.00 |
| Cmax ($\mu$g/mL) | 16.8 ± 1.70 | 25.1 ± 2.75 | 20.4 ± 1.23 | 25.2 ± 1.33 |
| AUC(0-inf) ($\mu$g.hr/mL) | 293 ± 53.8 | 524 ± 55.9 | 347 ± 51.2 | 549 ± 58.0 |
| AUC(0-last) ($\mu$g.hr/mL) | 281 ± 56.2 | 515 ± 52.9 | 342 ± 56.2 | 543 ± 60.4 |
| CL (mL/hr.kg) | 3.50 ± 0.589 | 1.93 ± 0.207 | 2.94 ± 0.489 | 1.84 ± 0.191 |
| T½ (hr) | 11.7 ± 0.96 | 16.6 ± 0.86 | 11.7 ± 0.535 | 14.0 ± 2.03 |
| Vss (mL/kg) | 65.8 ± 6.74 | 47.4 ± 3.28 | 55.2 ± 8.01 | 55.2 ± 8.01 |

TABLE 24

Total GW1843 Plasma Concentrations Following a Single 1 mg/kg Intravenous Bolus Dose of Liposome Encapsulated GW1843 (4:1 HSPC to Cholesterol Molar Ratio) in Male Sprague-Dawley Rats.

Concentration of Total GW1843 in Plasma ($\mu$g/mL)

| Time (hr) | Rat 1 | Rat 2 | Rat 3 | Rat 4 | MEAN | SD |
|---|---|---|---|---|---|---|
| 0.167 | 16.1 | 9.40 | 16.6 | 13.6 | 13.9 | 3.29 |
| 0.500 | 15.1 | 14.4 | 15.5* | 15.0* | 15.0 | 0.455 |
| 1.500 | 13.4 | 9.93 | 11.1 | 10.7 | 11.3 | 1.49 |
| 4.000 | 7.99 | 7.93 | 7.81 | 7.28 | 7.75 | 0.324 |
| 7.867 | 7.93 | 7.74 | 7.03 | 6.06 | 7.19 | 0.847 |
| 24.17 | 4.19 | 3.39⁺ | 3.23 | 3.21 | 3.51 | 0.464 |
| 32.43 | 2.83 | 2.53 | 1.66 | 2.53 | 2.39 | 0.505 |
| 47.83 | 1.10 | 0.616 | 0.425 | 0.921 | 0.766 | 0.302 |
| 72.37 | 0.137 | BLOQ | BLOQ | BLOQ | — | — |

BLOQ-Below limit of quantification
*Sample taken at 0.517 hr.
⁺Sample taken at 24.23 hr.

TABLE 25

Total GW1843 Plasma Pharmacokinetic Parameters, Obtained by Non-compartmental Analysis, Following a Single 1 mg/kg Intravenous Bolus Dose of Liposome Encapsulated GW1843 (4:1 HSPC to Cholesterol Molar Ratio) in Male Sprague-Dawley Rats.

| Animal Number Parameter | Rat 1 | Rat 2 | Rat 3 | Rat 4 | Mean | SD |
|---|---|---|---|---|---|---|
| Weight (kg) | 0.25719 | 0.25305 | 0.24655 | 0.24457 | 0.25034 | 0.005829 |
| AUC(0-inf) ($\mu$g.hr/mL) | 245 | 210 | 191 | 206 | 213 | 22.8 |
| AUC(0-last) ($\mu$g.hr/mL) | 243 | 201 | 187 | 189 | 205 | 26.1 |
| CL (mL/(hr.kg)) | 4.09 | 4.77 | 5.22 | 4.86 | 4.74 | 0.472 |
| Cmax ($\mu$g/mL) | 16.6 | 14.4 | 17.2 | 15.0 | 15.8 | 1.32 |
| MRT(0-inf)(hr) | 18.1 | 16.8 | 14.7 | 19.8 | 17.4 | 2.15 |
| T½ (hr) | 9.66 | 9.27 | 8.05 | 12.7 | 9.92 | 1.98 |
| Vss (mL/kg) | 73.8 | 80.3 | 76.7 | 96.0 | 81.7 | 9.90 |

TABLE 26

Summary of results comparing NX 1843 to free drug

| Drug/Dose | % Tumor Growth Inhibition (day 23) | % Regression (day 23) | Log Cell Kill |
|---|---|---|---|
| Vehicle control | 0 | 0 | 0 |
| 1843; 50 mg/kg; QD1-15 | 88.4 | 0 | 3.5 |
| 1843; 25 mg/kg; QD1-15 | 78 | 0 | 1.5 |
| NX1843; 7.5 mg/kg; QD2x7 | 97.5 | 83 | 4.6 |

TABLE 27

Summary of NX1843 dose-schedule comparison tumor response to combinations with 5-FU, NX211 and GW1843.

| Treatment | % TGI | % Regression day 22 | LCK | Cures |
|---|---|---|---|---|
| Control | 0 | 0 | 0 | 0 |
| NX1843, 25 mg/kg; QD1, 8 | 97 | 88 | 4.2 | 1 |
| NX1843, 15 mg/kg; QD1, 3, 5 × 2 | 95 | 86 | 3.2 | 1 |
| NX1843, 7.5 mg/kg; QD1-5 × 2 | 96 | 88 | 3.9 | 1 |
| GW1843, 100 mg/kg; QD1-5 × 2 | 80 | 0 | 2.4 | 0 |
| 5-FU, 100 mg/kg; QD1, 8 | 72 | 0 | 1.5 | 0 |
| NX211, 6 mg/kg; QD1, 8 | 78 | 0 | 1.9 | 0 |
| NX211, 6 mg/kg + 5-FU, 100 mg/kg; QD1, 8 | 78 | | 1.9 | 0 |
| NX211, 6 mg/kg + NX1843, 25 mg/kg; QD1, 8 | 97 | 89 | 3.4 | 2 |
| NX211, 6 mg/kg; QD1, 8 +GW1843, 100 mg/kg; QD1-5 × 2 | 91 | 50 | 3.4 | 0 |

TABLE 28

Summary of Dose Response Experiment with NX 1843.

| Drug and Dose | % TGI | % Regression | Cures |
|---|---|---|---|
| D5W Control | 0 | 0 | 0 |
| NX 1843; 25 mg/kg | 99 | 100 | 4 |
| NX 1843; 20 mg/kg | 97 | 100 | 2 |
| NX 1843; 15 mg/kg | 95 | 65 | 1 |
| NX 1843; 10 mg/kg | 92 | 58 | 0 |
| NX 1843; 5 mg/kg | 80 | 0 | 0 |

% TGI and Regression were determined on day 26, cures were determined at day 60.

TABLE 29

Antitumor Efficacy Results, Comparison of NX 1843 Formulations Dosed at 10 mg/kg, QD 1, 8 in the HCT-8 Xenograft model.

| NX 1843 Lot | % TGI | % Regression | Median LCK | Cures |
|---|---|---|---|---|
| AT-1084-86 | 91% | 18% | 2.44 | 0 |
| AT-1084-91B | 94% | 54% | 2.41 | 0 |
| AT-1084-95B | 93% | 56% | 3.32 | 0 |
| AT-1084-97B | 94% | 44% | 3.71 | 1 |
| SMC-1092-09 | 93% | 37% | 2.54 | 0 |

Rank analysis of variance demonstrated no significant differences between lots, p = 0.2985.

We claim:

1. A liposome comprising at least one phosphatidylcholine, a cholesterol, and (S)-2-(5-(((1,2-Dihydro-3-methyl-1-oxobenzo[f]quinazolin-9-yl)methyl)amino)-1-oxo-2-isoindolinyl)glutaric acid.

2. The liposome of claim 1 wherein said phosphatidylcholine is selected from the group consisting of distearoylphosphatidylcholine, hydrogenated soy phosphatidylcholine, soy phosphatidylcholine, egg phosphatidylcholine, hydrogenated egg phosphatidylcholine, dipalmitoylphosphatidylcholine, dioleoylphosphatidylcholine, dielaidoylphosphatidylcholine, and dimyristoylphosphatidylcholine.

3. The liposome of claim 2 wherein said phosphatidylcholine is hydrogenated soy phosphatidylcholine.

4. The liposome of claim 2 wherein said phosphatidylcholine is soy phosphatidylcholine.

5. The liposome of claim 2 wherein said phosphatidylcholine is dioleoylphosphatidylcholine.

6. The liposome of claim 2 wherein said phosphatidylcholine is dielaidoylphosphatidylcholine.

7. The liposome of claim 2 wherein said liposome further comprises phosphatidylglycerol.

8. The liposome of claim 7 wherein said hydrogenated soy phosphatidylcholine, cholesterol and phosphatidylglycerol are in a molar ratio of about 2:1:0.1.

9. The liposome of claim 3 wherein the hydrogenated soy phosphatidylcholine to cholesterol molar ratio is from about 5:1 to 2:1.5.

10. The liposome of claim 9 wherein said molar ratio is about 2:1.

11. The liposome of claim 9 wherein said molar ratio is about 4:1.

12. The liposome of claim 10 wherein said liposome is unilamellar and less than 100 nm.

13. The liposome of claim 12 wherein said hydrogenated soy phosphatidylcholine to (S)-2-(5-(((1,2-Dihydro-3-methyl-1-oxobenzo[f]quinazolin-9-yl)methyl)amino)-1-oxo-2-isoindolinyl)glutaric acid molar ratio is from about 5:1 to 75:1.

14. The liposome of claim 4 wherein the molar ratio of soy phosphatidylcholine to cholesterol is about 2:1.

15. The liposome of claim 5 wherein the molar ratio of dioleoylphosphatidylchoine to cholesterol is about 2:1.

16. The liposome of claim 6 wherein the molar ratio of dielaidoylphosphatidylcholine to cholesterol is about 2:1.

17. The liposome of claim 12 wherein said hydrogenated soy phosphatidylcholine to (S)-2-(5-(((1,2-Dihydro-3-methyl-1-oxobenzo[f]quinazolin-9-yl)methyl)amino)-1-oxo-2-isoindolinyl)glutaric acid molar ratio is from about 8:1 to 20:1.

18. A liposome comprising (S)-2-(5-(((1,2-Dihydro-3-methyl-1-oxobenzo[f]quinazolin-9-yl)methyl)amino)-1-oxo-2-isoindolinyl)glutaric acid, encapsulated in a liposome, wherein said liposome is comprised of hydrogenated soy phosphatidylcholine (HSPC) and cholesterol and wherein HSPC:cholesterol are in a molar ratio of about 2:1, and wherein the HSPC to (S)-2-(5-(((1,2-Dihydro-3-methyl-1-oxobenzo[f]quinazolin-9-yl)methyl)amino)-1-oxo-2-isoindolinyl)glutaric acid molar ratio is from 8:1 to 20:1, and wherein said liposome is unilamllar having a size of less than 100 nm.

19. The composition of claim 1 produced by the process comprising:
   a) forming a lipid film or powder comprised of phosphatidylcholine and cholesterol;

b) hydrating said lipid film or powder with an aqueous solution containing (S)-2-(5-(((1,2-Dihydro-3-methyl-1-oxobenzo[f]quinazolin-9-yl)methyl)amino)-1-oxo-2-isoindolinyl)glutaric acid;

c) applying energy whereby liposomes that are unilamellar and less than 100 nm are obtained;

d) cross-filtering against an aqueous solution to remove unencapsulated (S)-2-(5-(((1,2-Dihydro-3-methyl-1-oxobenzo[f]quinazolin-9-yl)methyl)amino)-1-oxo-2-isoindolinyl)glutaric acid whereby liposomes containing (S)-2-(5-(((1,2-Dihydro-3-methyl-1-oxobenzo[f]quinazolin-9-yl)methyl)amino)-1-oxo-2-isoindolinyl) glutaric acid are obtained.

20. The composition of claim 19 wherein said phosphatidylcholine is selected from the group consisting of distearoylphosphatidylcholine, hydrogenated soy phosphatidylcholine, soy phosphatidylcholine, egg phosphatidylcholine, hydrogenated egg phosphatidylcholine, dipalmitoylphosphatidylcholine, dioleoylphosphatidylcholine, dielaidoylphosphatidylcholine, and dimyristoylphosphatidylcholine.

21. The composition of claim 20 wherein said phosphatidylcholine is hydrogenated soy phosphatidylcholine.

22. The composition of claim 20 wherein said phosphatidylcholine is soy phosphatidylcholine.

23. The composition of claim 20 wherein said phosphatidylcholine is dioleoylphosphatidylcholine.

24. The composition of claim 20 wherein said phosphatidylcholine is dielaidoylphosphatidylcholine.

25. The composition of claim 20 wherein said liposome further comprises phosphatidylglycerol.

26. The composition of claim 19 wherein said energy is applied by a homogenizer.

27. The composition of claim 21 wherein the hydrogenated soy phosphatidylcholine to cholesterol molar ratio is from about 5:1 to 2:1.5.

28. The composition of claim 27 wherein said molar ratio is about 2:1.

29. The composition of claim 27 wherein said molar ratio is about 4:1.

30. The composition of claim 28 wherein said liposome is unilamellar and less than 100 nm.

31. The composition of claim 30 wherein said hydrogenated soy phosphatidylcholine to (S)-2-(5-(((1,2-Dihydro-3-methyl-1-oxobenzo[f]quinazolin-9-yl)methyl)amino)-1-oxo-2-isoindolinyl)glutaric acid molar ratio is from about 5:1 to 75:1.

32. The composition of claim 31 wherein said hydrogenated soy phosphatidylcholine to (S)-2-(5-(((1,2-Dihydro-3-methyl-1-oxobenzo[f]quinazolin-9-yl)methyl)amino)-1-oxo-2-isoindolinyl)glutaric acid molar ratio is from about 8:1 to 20:1.

33. The composition of claim 19 wherein said phosphatidylcholine is hydrogenated soy phosphatidylcholine (HSPC), and wherein said HSPC:cholesterol are in a molar ratio of about 2:1, and wherein the HSPC to (S)-2-(5-(((1, 2-Dihydro-3-methyl-1-oxobenzo[f]quinazolin-9-yl)methyl)amino)-1-oxo-2-isoindolyl)glutaric acid molar ratio is from 8:1 to 20:1.

34. A process for making liposomes comprising (S)-2-(5-(((1,2-Dihydro-3-methyl-1-oxobenzo[f]quinazolin-9-yl)methyl)amino)-1-oxo-2-isoindolinyl)glutaric acid, said process comprising:

a) forming a lipid film or powder comprised of phosphatidylcholine and cholesterol;

b) hydrating said lipid film or powder with an aqueous solution containing (S)-2-(5-(((1,2-Dihydro-3-methyl-1-oxobenzo[f]quinazolin-9-yl)methyl)amino)-1-oxo-2-isoindolinyl)glutaric acid;

c) applying energy whereby liposomes that are unilamellar and less than 100 nm are obtained;

d) cross-filtering against an aqueous solution to remove unencapsulated (S)-2-(5-(((1,2-Dihydro-3-methyl-1-oxobenzo[f]quinazolin-9-yl)methyl)amino)-1-oxo-2-isoindolinyl)glutaric acid, whereby liposomes containing (S)-2-(5-(((1,2-Dihydro-3-methyl-1-oxobenzo[f]quinazolin-9-yl)methyl)amino)-1-oxo-2-isoindolinyl) glutaric acid are obtained.

35. The process of claim 34 wherein said phosphatidylcholine is selected from the group consisting of distearoylphosphatidylcholine, hydrogenated soy phosphatidylcholine, soy phosphatidylcholine, egg phosphatidylcholine, hydrogenated egg phosphatidylcholine, dipalmitoylphosphatidylcholine, dioleoylphosphatidylcholine, dielaidoylphosphatidylcholine, and dimyristoylphosphatidylcholine.

36. The process of claim 35 wherein said phosphatidylcholine is hydrogenated soy phosphatidylcholine.

37. The process of claim 35 wherein said phosphatidylcholine is soy phosphatidylcholine.

38. The process of claim 35 wherein said phosphatidylcholine is dioleoylphosphatidylcholine.

39. The process of claim 35 wherein said phosphatidylcholine is dielaidoylphosphatidylcholine.

40. The process of claim 35 wherein said liposome further comprises phosphatidylglycerol.

41. The process of claim 34 wherein said energy is applied by a homogenizer.

42. The process of claim 36 wherein the hydrogenated soy phosphatidylcholine to cholesterol molar ratio is from about 5:1 to 2:1.5.

43. The process of claim 42 wherein said molar ratio is about 2:1.

44. The process of claim 42 wherein said molar ratio is about 4:1.

45. The process of claim 43 wherein said liposome is unilamellar and less than 100 nm.

46. The process of claim 45 wherein said hydrogenated soy phosphatidylcholine to (S)-2-(5-(((1,2-Dihydro-3-methyl-1-oxobenzo[f]quinazolin-9-yl)methyl)amino)-1-oxo-2-isoindolinyl)glutaric acid molar ratio is from about 5:1 to 75:1.

47. The process of claim 46 wherein said hydrogenated soy phosphatidylcholine to (S)-2-(5-(((1,2-Dihydro-3-methyl-1-oxobenzo[f]quinazolin-9-yl)methyl)amino)-1-oxo-2-isoindolinyl)glutaric acid molar ratio is from about 8:1 to 20:1.

48. The process of claim 34 wherein said phosphatidylcholine is hydrogenated soy phosphatidylcholine (HSPC), and wherein said HSPC:cholesterol are in a molar ratio of about 2:1, and wherein the HSPC to (S)-2-(5-(((1,2-Dihydro-3-methyl-1-oxobenzo[f]quinazolin-9-yl)methyl)amino)-1-oxo-2-isoindolinyl)glutaric acid molar ratio is from 8:1 to 20:1.

49. A method of inhibiting the growth of a tumor comprising the administration of a therapeutic or effective amount of the composition of claim 1 to a tumor.

50. The method of claim 49 wherein said tumor is drug resistant or drug sensitive.

51. The method of claim 49 wherein said tumor is from a cancer selected from the group consisting of ovarian, lung, colorectal, breast, head and neck, prostate, uteran, glioblastoma, and sarcoma.

52. The method of claim 51 wherein said phosphatidylcholine is selected from the group consisting of distearoylphosphatidylcholine, hydrogenated soy phosphatidylcholine, soy phosphatidylcholine, egg phosphatidylcholine, hydrogenated egg phosphatidylcholine, dipalmitoylphosphatidylcholine, dioleoylphosphatidylcholine, dielaidoylphosphatidylcholine, and dimyristoylphosphatidylcholine.

53. The method of claim 52 wherein said phosphatidylcholine is hydrogenated soy phosphatidylcholine.

54. The method of claim 52 wherein said phosphatidylcholine is soy phosphatidylcholine.

55. The method of claim 52 wherein said phosphatidylcholine is dioleoylphosphatidylcholine.

56. The method of claim 52 wherein said phosphatidylcholine is dielaidoylphosphatidylcholine.

57. The method of claim 52 wherein said liposome further comprises phosphatidylglycerol.

58. The method of claim 57 wherein said hydrogenated soy phosphatidylcholine, cholesterol and phosphatidylglycerol are in a molar ratio of about 2:1:0.1.

59. The method of claim 53 wherein the hydrogenated soy phosphatidylcholine to cholesterol molar ratio is from about 5:1 to 2:1.5.

60. The method of claim 59 wherein said molar ratio is about 2:1.

61. The method of claim 59 wherein said molar ratio is about 4:1.

62. The method of claim 60 wherein said liposome is unilamellar and less than 100 nm.

63. The method of claim 62 wherein said hydrogenated soy phosphatidylcholine to (S)-2-(5-(((1,2-Dihydro-3-methyl-1-oxobenzo[f]quinazolin-9-methyl)amino)-1-oxo-2-isoindolinyl)glutaric acid molar ratio is from about 5:1 to 75:1.

64. The liposome of claim 54 wherein the molar ratio of soy phosphatidylcholine to cholesterol is about 2:1.

65. The liposome of claim 55 wherein the molar ratio of dioleoylphosphatidylchoine to cholesterol is about 2:1.

66. The liposome of claim 56 wherein the molar ratio of dielaidoylphosphatidylcholine to cholesterol is about 2:1.

67. The method of claim 62 wherein said hydrogenated soy phosphatidylcholine to (S)-2-(5-(((1,2-Dihydro-3-methyl-1-oxobenzo[f]quinazolin-9-methyl)amino)-1-oxo-2-isoindolinyl)glutaric acid molar ratio is from about 8:1 to 20:1.

* * * * *